United States Patent [19]

Wissler

[11] Patent Number: 4,512,970
[45] Date of Patent: Apr. 23, 1985

[54] CHEMORECRUITINS OF LEUKOCYTES AND INFLAMED TISSUES

[75] Inventor: Josef H. Wissler, Bad Nauheim, Fed. Rep. of Germany

[73] Assignee: Max Planck Gesellschaft Zur Forderung der Wissenschaften, Gottingen, Fed. Rep. of Germany

[21] Appl. No.: 357,880

[22] Filed: Mar. 15, 1982

[30] Foreign Application Priority Data

Mar. 18, 1981 [DE] Fed. Rep. of Germany ....... 3110561

[51] Int. Cl.³ .................. A61K 39/395; A61K 37/02; C07G 7/00; C12P 21/00
[52] U.S. Cl. ............................. 424/85; 260/112 R; 435/68; 514/908; 514/885; 514/21
[58] Field of Search .................. 424/85, 177, 101; 260/112 R, 112 B; 435/68, 240, 241

[56] References Cited

PUBLICATIONS

Merriman C., et al., Proceeding of the Society for Experimental Biology and Medicine, vol. 149, pp. 782–784, 1975.
Lymphokines, editor Edgar Pick, Academic Press, vol. 2, pp. 1–19, 1981.
Fundamentals of Human Lymphoid Cell Culture, J. Leslie Glick, pp. 27–29, Marcel Dekker Inc., New York, 1980.
Fuderilp, O., Angew. Chemie, vol. 82, pp. 708–722, 1979.
Menkin V., "Biochemical Mechanisms in Inflammation", Charles C. Thomas, Springfield, IL, 1956 (Table of Contents Only).
Peirson, Am. J. Med. Tech., vol. 42, pp. 286–296, 1976.
Rother K., Eur. J. Immunol., vol. 2, pp. 550–558, 1972.
The United States Pharmacopeia, 19th Revision, U.S. Pharmacopeial Convention, Inc., Rockville, Md., p. 613, 1975.
Whiples H., et al., Ann. N.Y. Acad. Sci., vol. 113, pp. 511–1092, 1964.
Wissler J., Z. Physiol., vol. 361, pp. 1358–, 1980.
Gehbrehiwet B., J. Immunol., vol. 123, pp. 616–621, 1979.
Gordon, A. S., et al., Ann. N.Y., Acad. Sci., vol. 113, pp. 766–789, 1964.
Hayashi, I., Nature, vol. 259, pp. 132–134, 1976.
Iscove N., et al., J. Exp. Med., vol. 147, pp. 923–933, 1978.
Andersson J., J. Exp. Med., vol. 137, pp. 943–953, 1973.
Boggs D., Ann. Rev. Physiol., vol. 28, pp. 39–56, 1966.
British Pharmocopoeia 1973, 12th Ed., Appendix XIV I, 1973.
European Pharmocopoeia, vol. II, pp. 56–60, 1971.

*Primary Examiner*—Blondel Hazel
*Attorney, Agent, or Firm*—Cooper, Dunham, Clark, Griffin & Moran

[57] ABSTRACT

The invention relates to new chemorecruitins of leukocytes and inflamed tissue which have the biological and physicochemical properties stated in the patent claims. The compounds selectively induce a leukocytosis reaction and/or a leftward shift reaction in vivo. The invention also relates to a biotechnical process for preparing and isolating the chemorecruitins and to pharmaceutical compositions containing them.

35 Claims, 9 Drawing Figures

BIOLOGICAL EFFECTS OF MONOCYTO-LEUKORECRUITIN (ML R).
LONG-LASTING LEUKOCYTOSIS AND LEFTWARD SHIFT REACTION.

KINETICS OF CELL PATTERNS IN CIRCULATING BLOOD OF THE GUINEA
PIG UPON INTRAVENOUS ADMINISTRATION (T = 0) OF 25 pmol MLR/kg
GUINEA PIG.

■—■—■ TOTAL BLOOD LEUKOCYTE COUNT
▲—▲—▲ SEGMENTED (MATURE) NEUTROPHIL LEUKOCYTES
●—●—● NEUTROPHILIC BANDS AND METAMYELOCYTES

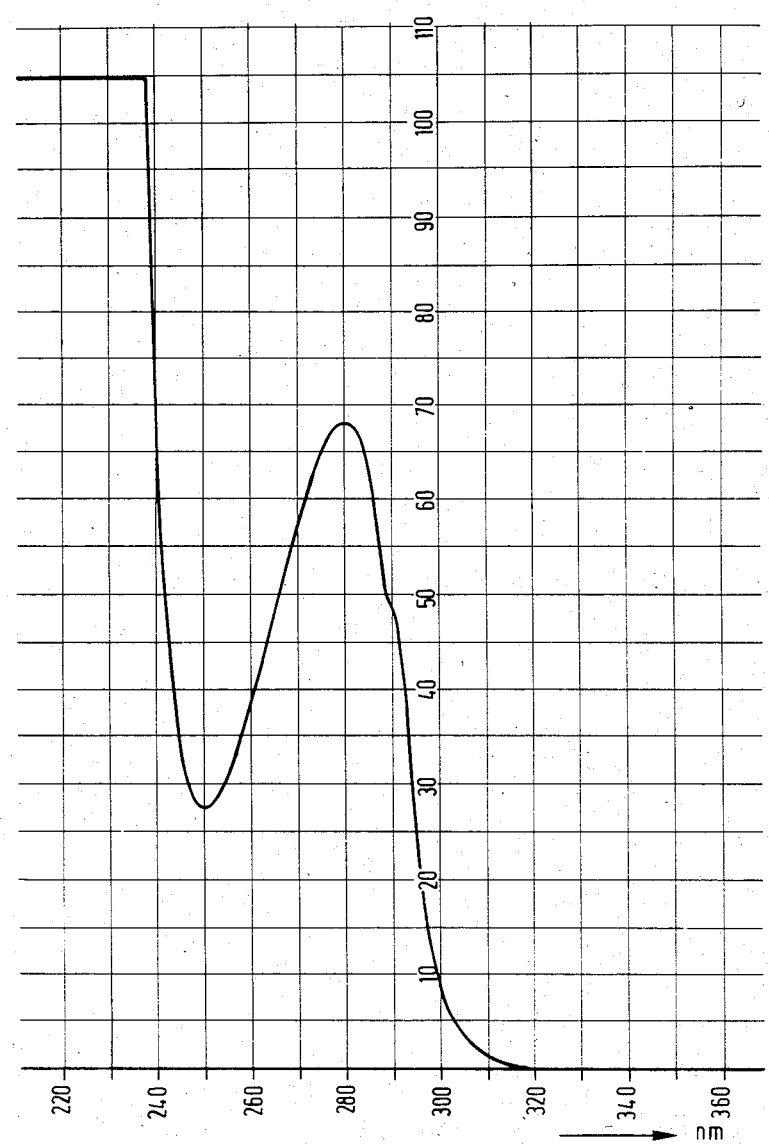
FIG. 2 ABSORPTION SPECTRUM OF THE MONOCYTO-LEUKORECRUITIN IN WATER AT 20°C AND EXTINCTION SCALE (0-100)
E = 0-2 AT LIGHT PATH d = 1 cm

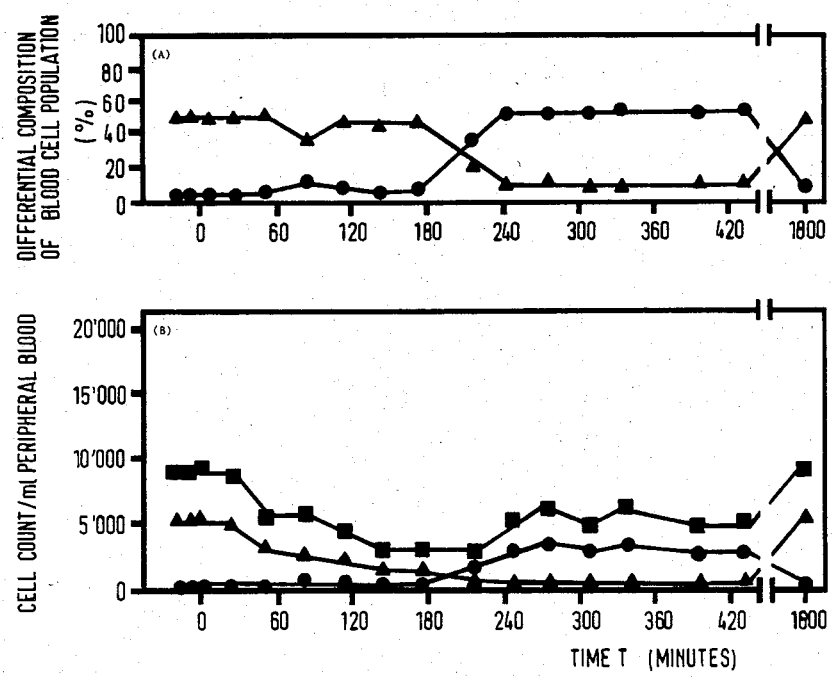

BIOLOGICAL EFFECTS OF MONOCYTO-METAMYELORECRUITIN (MMR): LEFTWARD SHIFT REACTION WITHOUT GENERAL LEUKOCYTOSIS REACTION.

KINETICS OF CELL PATTERNS IN CIRCULATING BLOOD OF THE GUINEA PIG AFTER INTRAVENOUS ADMINISTRATION (T = 0) OF 25 pmol MMR/kg GUINEA PIG.

■—■—■  TOTAL BLOOD LEUKOCYTE COUNT
▲—▲—▲  SEGMENTED (MATURE) NEUTROPHIL LEUKOCYTES
●—●—●  NEUTROPHILIC BANDS AND METAMYELOCYTES

FIG. 3

ABSORPTION SPECTRUM OF MONOCYTO-METAMYELORECRUITIN
IN WATER AT 20 C. EXTINCTION SCALE (0-100)
FIG. 4  E = 0-2 AT LIGHT PATH d = 1 cm

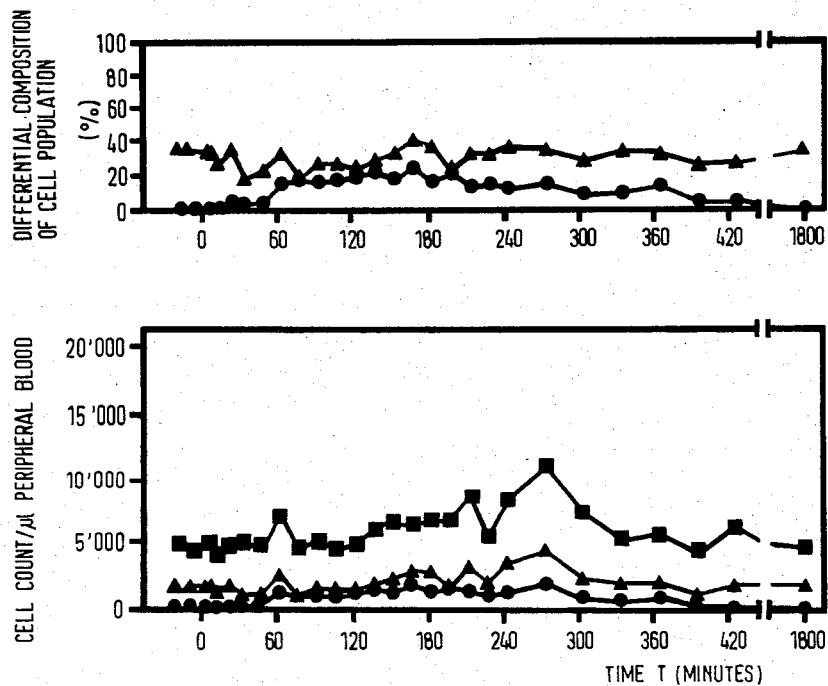

BIOLOGICAL EFFECTS OF GRANULOCYTO-METAMYELORECRUITIN (GMR):
LEFTWARD SHIFT REACTION WITH WEAK LEUKOCYTOSIS REACTION.

KINETICS OF CELL PATTERNS IN CIRCULATING BLOOD OF THE GUINEA
PIG AFTER INTRAVENOUS ADMINISTRATION (T = 0) OF 25 pmol GMR/kg
GUINEA PIG.

■—■—■ TOTAL COUNT OF LEUKOCYTES IN THE BLOOD
▲—▲—▲ SEGMENTED (MATURE) NEUTROPHIL LEUKOCYTES
●—●—● NEUTROPHILIC BANDS AND METAMYELOCYTES

FIG. 5

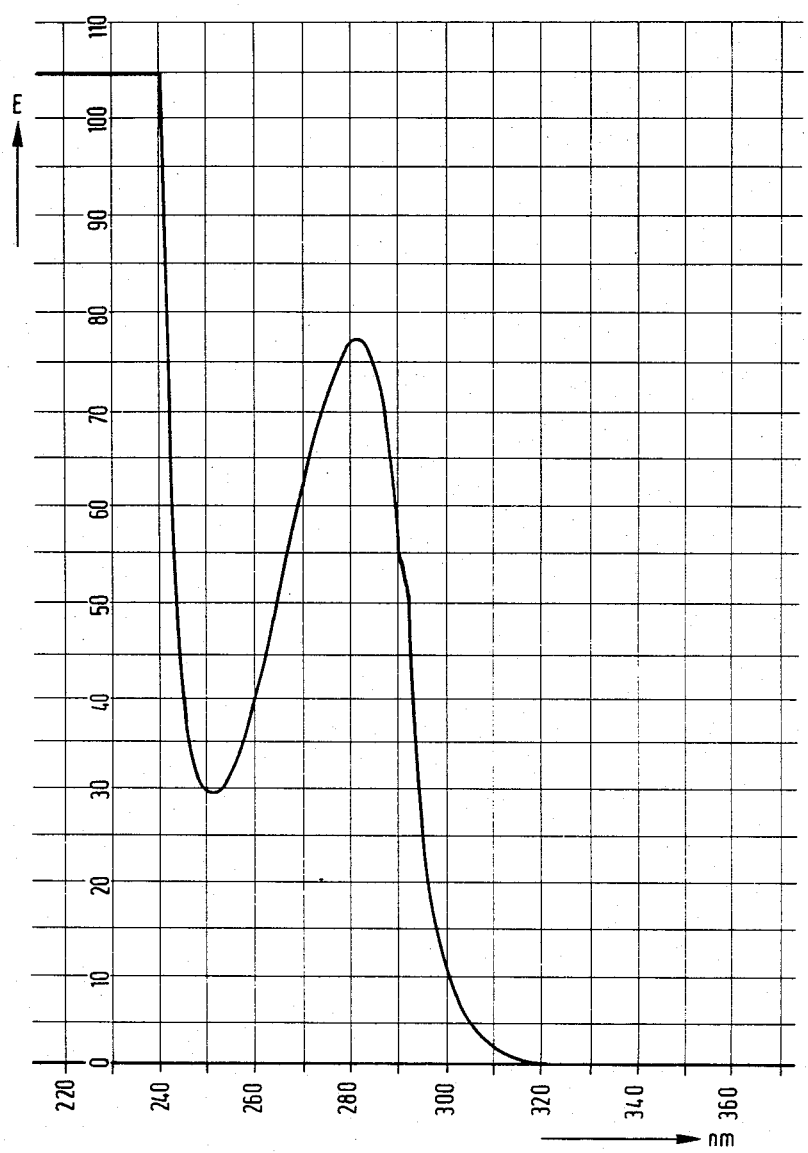
FIG. 6 ABSORPTION SPECTRUM OF THE GRANULOCYTO-METAMYELO-RECRUITIN AT 20°C. EXTINCTION SCALE (0-100) E = 0-2 AT A LIGHT PATH d = 1 cm STANDARD PYROGEN ASSAY ACCORDING TO EUR. PHARMACO-
POEIA 1975, VOL. II: RECTAL TEMPERATURE OF A RABBIT
PRIOR TO (V, A), DURING (*) AND AFTER (P) INTRAVENOUS
APPLICATION OF 10μg MONOCYTO-METAMYELORECRUITIN (MMR),
CORRESPONDING TO ABOUT 0.5 nmol MMR/kg ANIMAL.

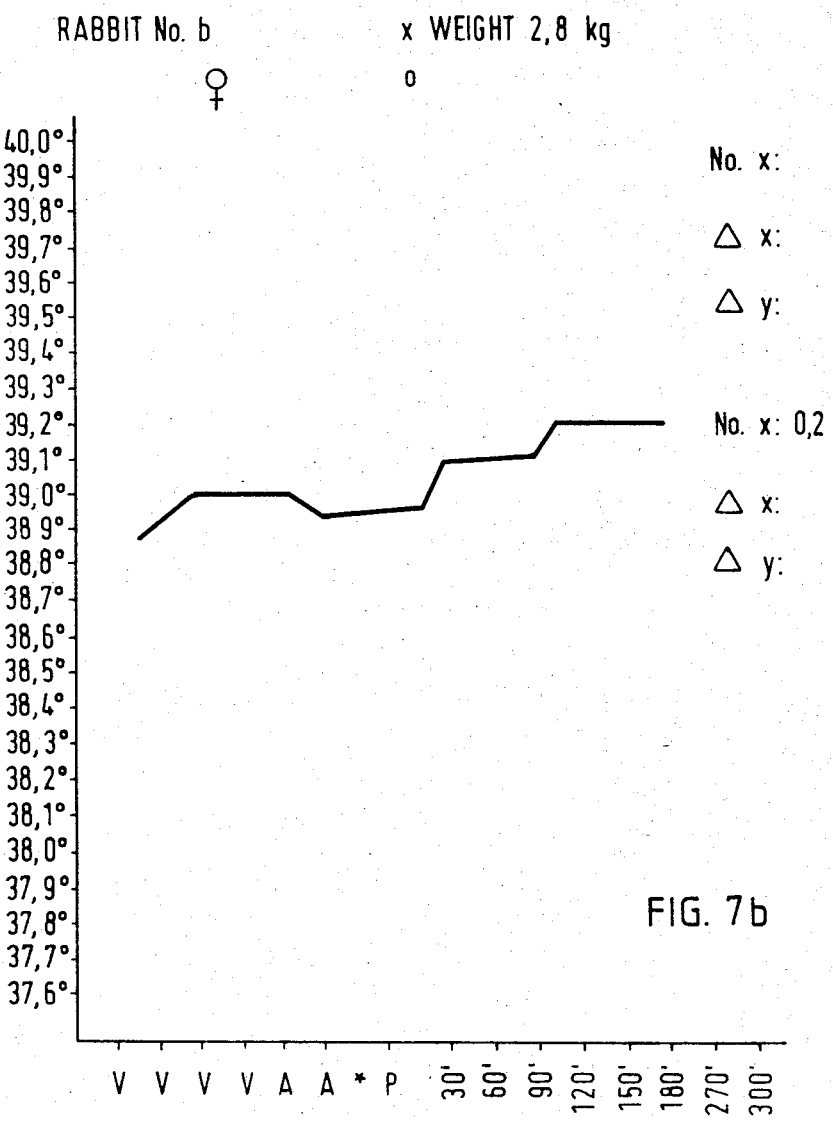
STANDARD PYROGEN ASSAY ACCORDING TO EUR. PHARMACO-
POEIA 1975, VOL. II: RECTAL TEMPERATURE OF A RABBIT
PRIOR TO (V, A), DURING (*) AND AFTER (P) INTRAVENOUS
APPLICATION OF 10μg MONOCYTO-METAMYELORECRUITIN (MMR),
CORRESPONDING TO ABOUT 0.5 nmol MMR/kg ANIMAL.

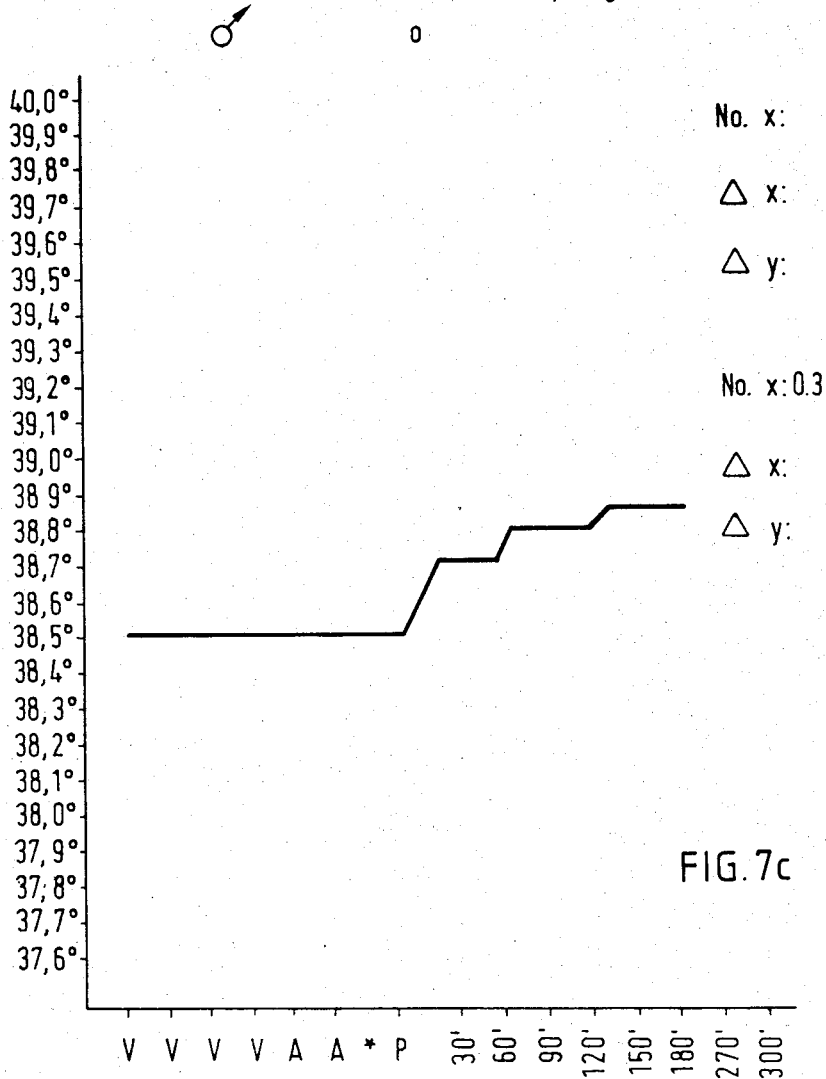
STANDARD PYROGEN ASSAY ACCORDING TO EUR. PHARMACO-
POEIA 1975, VOL. II: RECTAL TEMPERATURE OF A RABBIT
PRIOR TO (V, A), DURING (*) AND AFTER (P) INTRAVENOUS
APPLICATION OF 10μg MONOCYTO-METAMYELORECRUITIN (MMR),
CORRESPONDING TO ABOUT 0.5 nmol MMR/kg ANIMAL.

CHEMORECRUITINS OF LEUKOCYTES AND INFLAMED TISSUES

BACKGROUND OF THE INVENTION

The destruction of tissue in inflammation caused by non-immunological and immunological processes induces the formation of different endogenic substances (mediators and hormones). They regulate the complex steps of activation of the inflammation and tissue regeneration processes. The mediators are formed either by limited and regulated proteolysis of plasma and serum protein factors as humoral mediators; or they are liberated by active secretion and/or cell lysis from cells and tissues as cellular mediators. The mediators and hormones are especially important as specific carriers of chemical information which are formed and secreted by leukocytes in the course of cell proliferation processes (mitosis processes). They are components of the body's defence system whose systemic and local activation they regulate. The mediators contribute to the removal and detoxification of destroyed body's own components and/or intruded foreign components. In addition, by regulation of cell proliferation and tissue growth processes in wound-healing, they contribute to the restoration of physiological functions of the organism. As the classical hormones of endocrine glands, inflammatory mediators are trace components of tissues or blood and are present in very minute concentrations only. Experimental evidence shows that only up to 5,000 of such mediator protein molecules can be maintained in a steady state equilibrium by a cell in the mitotic cycle in its surrounding medium.

A reaction by which cells and organisms are mobilized and transferred by chemical substances from their production and storage sites to sites of functional readiness is defined as "chemorecruitment".

The mobilization of the different individual types of leukocytes and their precursors by chemical substances from their production and storage sites in the bone marrow and their recruitment into blood circulation is represented by two different reactions in vivo. These two reactions are typical classical reactions of pathology; see D. J. Boggs, Ann. Rev. Physiol. 28 (1966), p. 39 to 56; V. Schilling, ed., "Das Blutbild und seine klinische Verwertung", Gustav Fischer Verlag, Jena, 1929.

These reactions are the reactive increase in the number of circulating leukocytes (leukocytosis reaction) and the reactive change of the cell differential of individual circulating leukocyte types (leftward shift reaction). The latter is a result of the increase in the number of juvenile leukocytes. Several types of circulating leukocytes exist: Mature, fully differentiated granulocytes (segmented neutrophilic, eosinophilic and basophilic phagocytes) and mononuclear leukocytes (monocytic phagocytes and lymphocytes) with their different subpopulations (T, B-cells etc.). Of these circulating cells, only the mononuclear leukocytes are capable of further proliferation and differentiation. Precursors of these mature leukocyte types within the development and maturation line (hematopoesis) of the segmented granulocytes (leukopoesis) are immature cell types, namely the neutrophilic bands as well as adult and juvenile metamyelocytes which develop from the myelocyte, promyelocyte, myeloblast and the undifferentiated bone marrow stem cell. The names of the cells within such a development and maturation line are standardized today according to an international nomenclature; see E. L. Peirson, Amer. J. Med. Technol. 42 (1976) p. 288-296.

Endogenous chemical substances which activate and granulate such processes of cell development and maturation are called leukopoetins; see H. E. Whipple and M. I. Spitzer eds., Leukopoesis in Health and Disease, Ann. N.Y. Acad. Sci., 113 (1964), p. 511 to 1092. Leukopoetins which catalyze the release of the different leukocyte types and their precursors from the production and storage sites of the bone marrow into blood circulation are defined as "chemorecruitins" or "leukorecruitins". Their target is the barrier betweeen bone marrow production and storage sites on the one hand and blood circulation of the other hand.

The recruitment of leukocytes from the bone marrow is a characteristic in common to all inflammatory processes, e.g. in bacterial infections, tumors or myocardial infarction, etc.

The leukocytosis and leftward shift reactions are part of cybernetic loops of the body's defence system, which maintain the structural and functional readiness of the organism for tissue repair. Such reactions have often been used as diagnostic means in pathology. Apart from infarctions, immune reactions and mechanical tissue damage, other factors can lead to a leukocytosis reaction. Such factors are psychic stress and heavy meals.

Thus, chemorecruitment reactions must be divided into two different types: Mobilization of immature and mature leukocytes from production (poietic or primary) storage sites on the one hand; and recruitment from different (marginal or secondary) storage sites in tissues, e.g. the spleen, on the other hand. In the latter, mainly adult, mature cell types are recruited; see Boggs, loc. cit. Such leukocytes in secondary storage sites in tissues can also be activated, e.g. by cortisone; see Boggs, loc. cit. The mobilization of leukocytes from both storage sites can lead to a leucocytosis reaction. Therefore, an indication as to the kind of storage pool which has been activated can be obtained by distinguishing young immature and mature leucocytes; see Boggs, loc. cit.

Two negative feedback mechanisms have been postulated for the maintenance of the normal constant concentration and constant population differential of leukocytes in blood. One mechanism is supposed to be responsible for the production of the cells in the bone marrow, the other one for the release of the cells into the blood; see D. R. Boggs, loc. cit., H. E. Wipple and M. I. Spitzer, loc. cit. In these regulatory loops, humoral mediators are said to play a role; see V. Menkin, Biochemical Mechanisms in Inflammation, 2nd edition, Charles C. Thomas, Springfield, Ill., 1956.

V. Menkin, loc. cit. was the first to show that soluble tissue fractions participate in mechanisms which reactively increase the concentration of leukocytes in the blood above the normal range. He also isolated, from inflammatory exudates, a crystalizable substance whose nature has not been characterized in detail. However, the substance elicited a leukocytosis reaction in vivo.

Contamination with bacterial endotoxins presumably simulated part of the activities ascribed to the preparations; see Boggs, loc. cit. Such foreign substances as endotoxins are very effective in many respects on hematopoesis; see O. Lüderitz; Angew. Chemie 82 (1979), p. 708 to 722. Thus, it is known that, on the one hand, endotoxins can activate blood plasma protein systems (for instance the kinine and complement protein systems. On the other hand, they have a mitogenic effect on mononuclear leucocytes (B-cell mitogen); see J. Anderson et al., J. Exp. Med. 137 (1973), p. 943 to 953.

In the past, a major subject of research was the development of reliable in vitro test systems for leukocyte recruitment, the results of which would allow to be correlated to in vivo test systems of leukocytosis and leftward shift reactions. A. S. Gordon et al., Ann. N.Y. Acad. Sci., vol. 113 (1964), p. 766 to 789 developed such a laborious in vitro test system. With this system they obtained a humoral plasma factor inducing leukocytosis. Its nature was not elucidated in detail and its function must rather be considered part of the feedback mechanisms which can correct decreased blood leukocyte concentrations (leukopeniae) to normal. K. Rother, Eur. J. Immunol., vol. 2 (1972) p. 550 to 558 developed another, simpler in vitro test system to prove the mobilization of leukocytes from the bone marrow. In vivo, leukocytosis and leftward shift reactions are measured quantitatively by time-dependent periodic counting and differentiation of the different types of leukocytes in the blood after administration of the solution of the substance to be examined; see Schilling, loc. cit.

As a consequence of these findings, humoral serum proteins were prepared which induce the release of leukocytes from an isolate rat femur in vitro and a leukocytosis reaction in vivo. However, they were neither defined in more detail, nor are they molecularly uniform and/or biologically specific. Such a non-specifically acting humoral serum protein was for instance prepared by B. Gehbrehiwet and J. H. Müller-Eberhardt, J. Immunol., vol. 123 (1979), p. 616 to 621, by cleaving a preparation of the complement component C3 by means of trypsin.

A natural humoral leukocyte-recruiting protein ("serum-leukorecruitin") which is different therefrom and which has biological and topochemical specificity, was prepared from contact-activated serum by J. H. Wissler et al. Z. Physiol. 361 (1980) p. 1358.

All above-described preparations for the induction of the leukocytosis reaction are serum-derived (humoral) chemical substances. Cellular mediators (wound hormones), i.e. mediator substances secreted by cells, which cause a leukocytosis reaction (chemorecruitins) have not yet been described. Furthermore, mediator substances (chemorecruitins)—either of humoral or cellular origin—which induce a leftward shift reaction are not known at all.

It is therefore a primary object of this invention to provide a new class of cellular chemorecruitins from leukocytes.

It is another object of this invention to provide a new class of cellular chemorecruitins from leukocytes in highly purified form.

It is another object of this invention to provide a new class of cellular chemorecruitins from leukocytes in physical quantities for practical use.

It is another object of this invention to provide a new class of chemorecruitins from leukocytes, which represent biologically specific, active and naturally acting mediators of the leukocytosis and/or leftward shift reactions.

It is another object of this invention to provide a new class of chemorecruitins from leukocytes, which are suitable for specifically influencing the defense state of mammalian (e.g. human) organisms.

It is still another object of this invention to provide a process for producing and obtaining a new class of chemorecruitins from leukocytes in an economical, biotechnically useful and relatively simple manner.

It is still another object of this invention to provide a process for producing and obtaining a new class of chemorecruitins from leukocytes in a highly purified, molecularly homogenous form and in physical quantities for practical use.

It is still another object of this invention to provide a pharmaceutical composition for specifically influencing the defence state of the body of mammalians.

These and other objects and advantages of the present invention will be evident from the following description of the invention.

SUMMARY OF THE INVENTION

The subject matter of the invention are chemorecruitins of leukocytes and inflamed tissue which are characterized by the following properties:
(a) biological activity in vivo and in vitro:
  specific induction of selective positive leukocytosis and/or leftward shift reactions by recruitment of mature and juvenile leukocytes from the bone marrow into the blood in vivo and in vitro;
  positive mobilization of mature and juvenile leukocytes directly from the bone marrow in vitro (also in bloodfree systems, for instance cell culture and salt solutions);
  they are substantially free of other biological effects;
(b) physico-chemical properties:
  no protein quaternary structure in the form of physically bound peptide subunits: each of the native proteins consists of only one peptide unit;
  electrophoretic migration in acrylamide matrices at a pH of 7.40 is anodic;
  soluble in aqueous media including in 15% ethanol at a pH value of at least 4.0 to 10;
  constant temperature coefficient of solubility in ammonium sulfate solutions between $-10°$ C. and $+50°$ C.;
  they contain, amongst others, the amino acids tyrosine, phenylalanine, alanine, glycine, lysine, valine, glutamic acid, arginine, leucine;
  they adsorb reversibly in structure and biological activity on anion and cation exchangers, calcium phosphate gel and hydroxyapatite and can be subjected in native form to volume partition chromatography.

The chemorecruitins of leukocytes evaluated for the first time and obtained in highly purified form in this invention are further characterized by the fact that they are substantially free of other biological effects. More particularly, the chemorecruitins of the invention do not show:
  capillary permeability-enhancing activity in the skin test;
  spasmogenic effects on smooth muscles;
  spasmogenic effects on striated muscles;
  endotoxin content and endotoxin-like or similar activities;
  chemical attraction effects (chemotaxis) of leukocytes in vitro;
  positive or negative chemokinetic effects on leukocytes in vitro;
  phagocytosis-stimulating effects on leukocytes in vitro;

blood clot-inducing activities alone or in the presence of plasma;

apparent shock or other systemically detrimental effects of the immediate or protracted type on the intact organism of mammals in vivo;

significant pyrogenic effect in vivo;

lysis effects in vitro on erythrocytes, thrombocytes and leukocytes;

phlogistic activity in situ;

induction of vascularization of tissues (cornea) by chemotropism;

mitogenic effects in vitro on bone marrow leukocytes, peripheral and tissue leukocytes;

chalone effects in vitro on bone marrow leukocytes and blood and spleen mononuclear cells;

chalone effects on endothelial cells of arterial vessels.

DETAILED DESCRIPTION OF THE INVENTION

Figure 1:
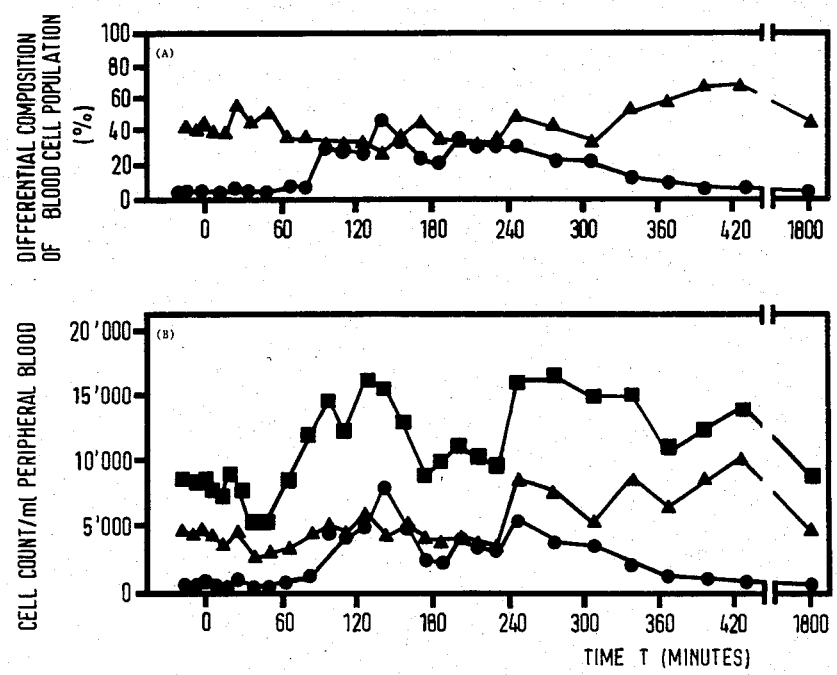

The chemorecruitins of the invention have typical protein properties and protein reactions (folin and biuret reactions). Their melting point is at approximately 200° C. (decomposition in an air and oxygen-free atmosphere).

The chemorecruitins of the invention are cellular inflammatory mediators with topobiochemically and biologically specific activity directed to specific target cells of the bone marrow which are remote from the site of inflammation. Their biological tasks are the specific recruitment of mature and juvenile bone marrow leukocytes into the blood (leukocytosis reaction and/or leftward shift reaction). These leukopoietins are not normal independent blood or serum components. Apart from many other hormones and mediators, they are formed in vitro in leukocyte cultures or in vivo with the accumulation of leukocytes at the site of inflammation.

The chemorecruitins of the invention differ from the structural and functional properties of the bacterial endotoxins in many of their chemical and biological properties: As inflammatory mediator proteins, the chemorecruitins have no local phlogistic effect at the site of inflammation. As the known hormones of endocrine glands, the chemorecruitins formed by cells (leukocytes) act as specific chemical signals only on target cells remote from the reaction site of their formation and represent true wound hormones: Their specific information is not transmitted by autocrine or paracrine, but by endocrine mechanisms from the site of their formation (reaction site of inflammation) through blood circulation to the remote reception site (bone marrow). There they act on specific types of stored leukocytes which are chemically mobilized and recruited into circulation. Chemical mobilization of stored leukocytes follows mechanisms distinctly different from chemotaxis and chemokinesis.

Consequently, chemorecruitins induce a leukocytosis reactions by recruitment of new bone marrow leukocytes and/or a leftward shift reaction by selective recruitment of juvenile leukocytes into the blood in vivo or into culture solutions and blood substitutes in vitro.

In addition other molecular properties of the inventive chemorecruitins, especially their low blood levels necessary for their activity, also indicate similarities of these inflammatory mediators to hormones. These effective low concentrations are comparable to effective blood insulin concentrations. The active threshold doses range from approximately 1 to 10 pmols of chemorecruitin/kg of test organism. This corresponds to a calculated concentration of approximately 30 pmols of protein/l of blood. An $LD_{50}$ value cannot be measured, since no lethal effects have been observed even with doses 10,000 times the amount of the physiologically active (leukocyte-recruiting)threshold dose.

The activity of the inventive chemorecrutins can be demonstrated in vitro by the rat femur test according to K. Rother, loc. cit. (1972) as well as in vivo. In this latter test, the kinetics of the leukocytosis and or leftward shift reactions are measured in blood (vena saphena sinistra) and in the sternum bone marrow of the guinea pig before and after intravenous injection (vena saphena dextra) of chemorecruitin probes.

The inventive chemorecruitins can be divided into two classes: Compounds which recruit a mixed leukocyte population from the storage sites into circulation are called leukorecruitins. Compounds which recruit specific types of leukocytes from the bone marrow into blood circulation are termed according to the corresponding cell type which they recruit, e.g. metamyelorecruitins, monorecruitins. or lymphorecruitins.

Normally, leukorecruitin hormones mobilize the different mature leukocyte types jointly. The portion of immature (juvenile) leukocyte types can differ during recruitment reaction and depends on the chemorecruitin itself. The chemically induced leukocytosis reaction may or may not be coupled with a leftward shift reaction of varying intensity. In the text below, the leukorecruitins are exemplified by means of the compound which is derived from monocytes and accordingly called monocyto-leukorecruitin (MLR).

Apart from or addition to the above-mentioned properties which chemorecruitins have in common, the MLR has the following specific properties:

(a) biological effects in vivo:
  induction of prolonged, strong leukocytosis reactions with leftward shift reaction and a late monocytosis and eosinophilla phase according to FIG. 1;

(b) physico-chemical properties:
  molecular weight of the native protein (primary structure); approximately 12,000 dalton;
  insoluble in an ammonium sulfate solution at 90% saturation (3.6 mol/l);
  absorption spectrum (UV, visible and near IR-range) as given in FIG. 2.
  extinction coefficients according to the following Table I:

TABLE I

| wave length, nm | $E_1$ mg/ml, 1 cm (H2O, 20° C.) ± 6% |
|---|---|
| 250 (min) | 0.28 |
| 260 | 0.38 |
| 270 | 0.55 |
| 280 (max) | 0.68 |
| 290 | 0.48 |
| 400–1000 | 0 |
| $E_{280}/E_{260}$ | 1.78 |

The MLR is secreted by monocytes. Its formation can be induced by mitogenic actions on cells such as by polyvalent lectin mitogens from *Canavalia ensiformis* (Concanavalin A=CON), endotoxin action or cellular immune reactions.

The inventive chemorecruitins which recruit specific leukocyte types can have a double effect. They recruit a specific type of leukocytes into circulation and may sequestrate another circulating one. This type of chemorecruitins will be exemplified by two different metamyelorecruitins.

The metameylorecruitins can be derived e.g. from monocytes or granulocytes. Accordingly, they are termed monocytometamyelorecruitin (MMR) and granulocyto-metalmyelorecruitins (GMR), respectively.

The double effect of some metamyelorecruitin consists in that immature juvenile leukocyte forms of the granulocyte development line, e.g. mainly juvenile and mature metamyelocytes and neutrophilic bands, are recruited into circulation, whereas circulating mature cell types of this line, e.g. segmented neutrophilic bands are sequestrated. Consequently, this type of chemorecruitin action is a strong leftward shift reaction accompanied by only a weak or no leukocytosis reaction. Even an accompanying leukopenia reaction may be the result of this chemorecruitin action.

Apart from or additionally to the above-mentioned properties which chemorecruitins have in common, MMR has the following special properties:

(a) biological activities in vivo:
   induction of specific leftward shift reaction by recruitment of juvenile leukocytes and sequestration of mature leukocytes according to FIG. 3 and Table II;
   no general leukocytosis reaction;

(b) physico-chemical properties:
   molecular weight of the native protein (primary structure): approximately 6,500 daltons;
   soluble in saturated ammonium sulfate solution (4.0 mol/l);
   absorption spectrum (UV, visible and near IR-range) according to FIG. 4;
   extinction coefficient according to Table III

TABLE III

| wave length, nm | $E_{1\ mg/ml,\ 1\ cm\ (H_2O,\ 20°\ C.)} \pm 6\%$ |
|---|---|
| 250 (min) | 0.23 |
| 260 | 0.32 |
| 270 | 0.50 |
| 280 (max) | 0.59 |
| 290 | 0.42 |
| 400–1000 | 0 |
| $E_{280}/E_{260}$ | 1.84 |

As with MLR, the MMR is secreted by monocytes, and its formation can be induced by mitogenic actions on cells, e.g. by lectins, endotoxins or cellular immune reactions.

Apart form or additionally to the above-mentioned properties, which chemorecruitins have in common, GMR has the following special properties:

(a) biological activities:
   induction of leftward shift reaction with late, short-lasting monocytosis and weak leukocytosis reaction according to FIG. 5;

(b) physico-chemical properties:
   molecular weight of the native protein (primary structure): approximately 15,000 dalton;
   insoluble in a 90% saturated ammonium sulfate solution (3.6 mol/l);
   absorption spectrum (UV, visible and near IR-range) as given in FIG. 6;
   extinction coefficient according to the following table IV;

TABLE IV

| wave length, nm | $E_{1\ mg/ml,\ 1\ cm\ (H_2O,\ 20°\ C.)} \pm 6\%$ |
|---|---|
| 252 (min) | 0.23 |
| 260 | 0.32 |
| 270 | 0.49 |
| 280 (max) | 0.62 |
| 290 | 0.44 |
| 400–1000 | 0 |
| $E_{280}/E_{260}$ | 1.92 |

The GMR is secreted by granuloctes. Its formation is already induced by removal of cells from their physiological environment (blood circulation), e.g. by emigration into tissue. Therefore, a stimulation by addition of mitogens is not necessary in this case.

Up to a non-physiological concentration of 10 μmols/l the inventive chemorecritins neither display chemotactic nor chemokinetic nor phagocytic nor mitosis-stimulating activity for neutrophil, eosinophil and mononuclear leukocytes of man, rabbit, pig, dog, guinea pig or rat. Furthermore, they have no spasmogenic activity on smooth muscles of guinea pig ileum and no capillary permeability-enhancing activity in the skin test in guinea pigs using Evans blue as intravenously injected marker. Finally, they do not have apparent shock activity even when intravenously applied to guinea pigs or rabbits in doses up to 10,000 times the biologically active amount. Nor do they have a pyrogenic effect in rabbits based on the standardized method by rectal temperature measurement in accordance with the European Arzneibuch (Europ. Pharmacopoeia) vol. II, 1975, pa. 56 to 59, British Pharmaceopoeia 1973 p.A. 115, Appendix XIV I and U.S. Pharmacopoeia 1975 19th revision, p. 613 (U.S. Pharmacopoeia Convention, Rockville, Md.). Nor is any other systemic biological reaction detectable after intravenous administration of a high dose of 0.1 mg/kg (about 10 nmol/kg) in guinea pigs and rats.

In FIGS. 1, 3 and 5 and in Table II, induction of leukocytosis and leftward shift reactions in guinea pigs by administration of MLR, MMR and GMR are schematically represented. The figures show time-dependently the total counts and types of granulocytes in blood after administration of 25 pmol of chemorecruitins per kg test animal at the time t=0. The readings were taken in intervals of about 3 to 30 minutes over a period of 24 hours by counting and differenciating the leukocytes present in a certain blood volume (10 nl).

TABLE II

Kinetics of cell patterns in circulating blood of guinea pigs after intravenous administration of 25 pmol monocyto-metamyelorecruitin/kg guinea pig

| Time, h | 0.0 | 0.5 | 3.0 | 4.0 | 5.0 | 6.0 | 20.0 |
|---|---|---|---|---|---|---|---|
| Segmented neutrophilic leukocytes, cells/ml ± 10% | 5040 | 2538 | 1444 | 530 | 432 | 500 | 4785 |
| Rod-shaped neutrophilic leukocytes cells/ml ± 10% | 90 | 282 | 646 | 3021 | 2880 | 3000 | 261 |

In FIGS. 2, 3 and 6, UV-absorption spectra of MLR, MMR and GMR dissolved in water at 20° C. are represented. The extinction scale (0–100), E=0 to 2 is given for an optical path of d=1 cm.

Figure 7A:
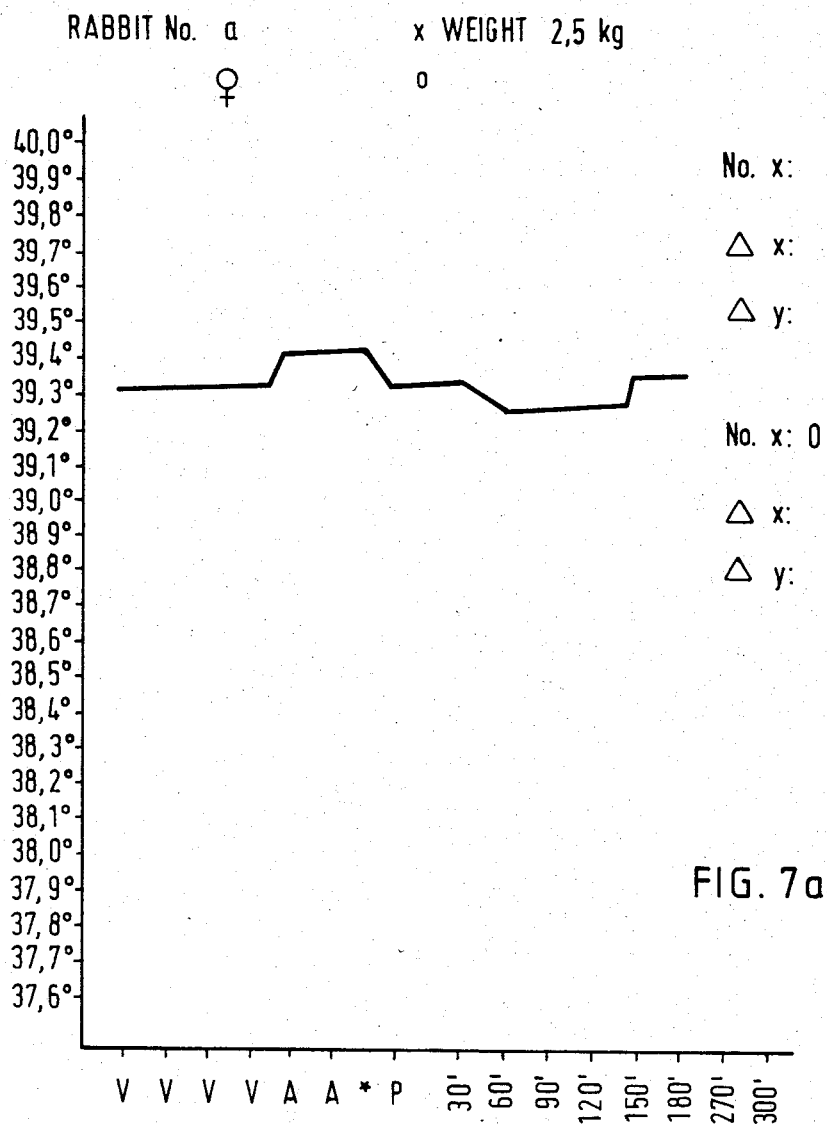

FIG. 7 shows a standard pyrogen test performed in accordance with the 1975 edition of the European Pharmacopoeia. It is carried out with three different rabbits (a,b and c) having an average weight of about 3 kg. Intravenous administration of porcine MMR in an amount of 1 µl (10 µg) per animal (=about 0.5 nmol MMR/kg animal) in 1 ml (0.9 w/v%) physiological saline shows no positive effect. This amount of MMR represents about 500 times the biologically active (leukocyte recruiting) threshold dose. The diagrams in FIG. 7 are graphs of the curves of the rectal temperature in the rabbit before (A), during (*), shortly after (P) and in addition, 30 to 160 minutes after application.

The 1975 edition of the European Pharmacopoeia, the British (1973) and the American (USP) (1975) Standards allow the designation "pyrogen-free" to be applied to preparations for which the sum of the fluctuations of the rectal temperature in a total of three experimental rabbits dose not exceed the value of 2.6° C. and, in particular, is below 1.15° C. The experimental results given in FIG. 7 fulfills these criteria. According to these definitions, the MMR-preparation is pyrogen-free and without febrile activity. This also applies to the highly purified MLR and GMR preparations. This extremely sensitive criterion for contamination of proteins with bacterial endotoxins and other ubiquitous pyrogens demonstrates the great efficacy of the process of the purification of the cellular chemorecruitins of the invention. It is an obvious parameter for the biological specificity of chemorecruitins.

The leukocyte-derived chemorecruitins prepared and obtained according to the invention are valuable, endogenous and active protein substances that can be used to act specifically on the defence state of the body, e.g. the immune status. They are useful for specific influence on leukocytosis and leftward shift reactions and also for leukocyte functions, for instance in inflammatory reactions, tumors, mycoses and myocardial infarctions. In addition, the chemorecruitins can be used to prepare antibodies against them for specifically influencing the course of leukocyte recruitment in leukemia. Further applications of chemorecruitins are for specific diagnosis and therapy of distinct states of leukopenia. Moreover, chemorecruitins and their antibodies, respectively, can be used as diagnostic means for investigating monocyte-dependent leukemia of so far unknown origin.

For these purposes, the chemorecruitins are administered parentally and preferably intravenously in normal pharmacological forms to mammalians, e.g. humans, in a daily dose of 1 to 100 pmol/kg.

Another subject matter of the invention is a process for the biotechnical preparation and isolation of chemorecruitins from leukocytes and from inflamed tissue sites. It is characterized in that either the leukocytes or the inflamed tissue are homogenized; or that leukocytes are cultured and the chemorecruitins formed or liberated are isolated from the homogenates or from the supernatant culture solution.

In principle, it is possible to prepare mediators from leukocytes directly without cell cultures. However, such a procedure is not economical: The leukocytes are destroyed by the process; the yields in mediators are low, since their synthesis and secretion is not stimulated prior to isolation; the mediators can be contaminated by intracellular structural constituents of leukocytes. Therefore, in the process of the invention, it is preferred to isolate the chemorecruitins from the supernatant solution of the leukocyte culture. In principle, the leukocytes can be cultured in any leukocyte-compatible medium.

For the culture of different cell types, such as bone marrow cells, heart muscle cells or leukocytes, different culture media are known. These media normally are aqueous solutions which contain numerous different compounds. Main constituents of these culture media are salts, sugars and metabolites, amino acids and derivatives, nucleosides, vitamins, vitaminoids, coenzymes, steroids, antibiotics and other additives, such as tensides, heavy metal salts and indicator dyes. Special examples of known culture media are named "HAM", "MEDIUM 199" and "NCTC", see H. J. Morton, In Vitro 6 (1970) p. 89 to 108.

When culturing cells for more than one hour, as in the case of leukocytes, mostly serum (e.g. fetal calf serum or horse serum) is added to the culture medium. The serum constituents are said to be favourable for the maintenance of cellular functions. However, if the serum-containing culture solution is to be subjected to processes for isolating proteins (mediators) which are formed by culturing cells, the preparation of trace protein products is difficult for reasons of the multipilicity of compounds making up the complex mixture of serum added to the culture. In addition, under such conditions, upon addition of serum to a cell culture medium, it is difficult if not at all impossible to recognize the origin of the mediators: It is then an open question whether or not a distinct mediator is of humoral (serum) or cellular (leukocyte) origin and from which species this mediator stems. Thus, the mediator may be derived from the species whose cells have been cultured; or, alternatively, it may be derived from the species from which the added (mostly heterologous) serum stems.

Besides serum-containing culture media, serum-free, synthetic media are also known; see H. J. Morton, loc. cit; I. Hayashi and G. H. Sato, Nature 259 (1976) p. 132–134; N. N. Iscove and F. Melchers, J. Exp. Med. 147 (1978) p. 923–933.

However, these known media likewise have drawbacks for both the culture of cells and for the preparation of the mediators formed from the culture supernatant. The tensides, heavy metal salts and/or dyes contained therein may damage or irreversibly contaminate the trace mediator proteins.

On the other hand, such known serum-free media are devoid of essential constituents which are necessary for maintaining the structural and functional viability of leukocytes. Therefore, none of the culture media known so far can be suitably used for the culture of leukocytes and the biotechnical preparation of cellular trace components, such as chemorecruitins.

For the culture of leukocytes, a new, fully synthetic chemically defined culture medium is preferably used. It provides favourable conditions for cell culture and facilitates the preparation and isolation of the cellular chemorecruitin proteins from the culture supernatant.

The fully synthetic, chemically defined cell culture medium preferably used in this invention contains the normal groups of compounds, such as salts, sugars, polyols, uronic acids, and derivatives, amino acids and derivatives, nucleosides and nucleoside bases, vitamins, vitaminoids, phytyl derivatives, coenzymes and steroids in aqueous solution. It is characterized in that it additionally contains one or a mixture of several compounds which so far have not been considered for use in cell culture media. These are especially valuable for expression of the life functions, for the proliferation of leukocytes and for promoting their capability to produce mediators. These substances include unsaturated fatty acids, flavanoids, ubiquinone, vitamin U, mevalolactone and L-carnosine.

In prolonged leukocyte culturing, the cell culture medium is preferably used without addition of serum. Instead, it contains at least one defined protein.

In further preferred embodiments of the invention, the synthetic, serum-free cell culture medium used in this invention may contain additional compounds, e.g. polyhydroxy compounds and sugars, amino acids, nucleosides, anionic compounds and/or vitamins which are not common in the known culture media. These compounds are useful in culturing leukocytes. The constituents in the culture medium used in this invention are equilibrated in their ratios so that their concentrations mainly correspond to the natural concentration ranges of the plasma; see Ciba-Geigy AG (editor) (1969) in Documenta Geigy, Wissenschaftliche Tabellen seventh edition, Geigy S. A. Basle.

Preferably, the cell culture medium is free of tensides, heavy metal salts and dye indicators which can damage the cells and may have a detrimental effect on the isolation of the desired cell products.

The exact composition and the properties of the new cell culture medium are described in the patent application Ser. No. 358,045 filed simultaneously on the basis of West German Patent Application No. P 31 10 559.9.

The cell culture medium with the composition given in Table V below is especially preferred in the process of the invention for culturing leukocytes.

The medium is prepared with water of ASTM-1-quality; see ASTM D-1193-70 Standard Specification for Reagent Water 1970; Annual Book of ASTM-Standards, Easton, Md., ASTM 1970. In addition, it is freed from possible endotoxin-contaminations by ultrafiltration on tenside-free membranes with an exclusion limit of 10,000 dalton. The resulting medium is sterilized by filtration on tenside-free membranes with a pore size of 0.2 μm.

TABLE V

| No. | Component | mol/l |
|---|---|---|
| 1 | Disodium hydrogenphosphate | 0.8 m |
| 2 | Potassium dihydrogenphosphate | 0.2 m |
| 3 | Potassium chloride | 5.0 m |
| 4 | Sodium chloride | 120.0 m |
| 5 | Sodium sulfate | 0.2 m |
| 6 | D-Glucose | 5.0 m |
| 7 | L-Ascorbic acid (C) | 0.2 m |
| 8 | Choline chloride | 50.0μ |
| 9 | 2-Deoxy-D-ribose | 5.0μ |
| 10 | D-Galactose | 0.5 m |
| 11 | D-Glucurono-γ-lactone | 0.1 m |
| 12 | Glycerol | 50.0μ |
| 13 | Myo-inositol | 0.5 m |
| 14 | Sodium acetate | 0.2 m |
| 15 | Sodium citrate | 50.0μ |
| 16 | Sodium pyruvate | 0.1 m |
| 17 | D-Ribose | 20.0μ |
| 18 | Succinic acid | 0.1 m |
| 19 | Xylitol | 10.0μ |
| 20 | D-Xylose | 20.0μ |
| 21 | Calcium chloride | 2.0 m |
| 22 | Magnesium chloride | 1.0 m |
| 23 | Sodium hydrogencarbonate | 10.0 m |
| 24 | Serum albumin (human) | 7.7μ |
| 25 | L-Asparagine | 0.1 m |
| 26 | L-Glutamine | 1.0 m |
| 27 | Adenosine | 50.0μ |
| 28 | 4-Aminobenzoic acid | 2.0μ |

TABLE V-continued

| No. | Component | mol/l |
|---|---|---|
| 29 | L-Aspartic acid | 0.1 m |
| 30 | D-Biotine (Vitamin H) | 1.0μ |
| 31 | Cytidine | 50.0μ |
| 32 | L-Glutamic acid | 0.1 m |
| 33 | L-Isoleucine | 0.2 m |
| 34 | 5-Methylcytosine | 5.0μ |
| 35 | L-Phenylalanine | 0.1 m |
| 36 | Riboflavine (B2) | 1.0μ |
| 37 | Thymine (5-methyluracil) | 5.0μ |
| 38 | L-Tryptophane | 50.0μ |
| 39 | L-Tyrosine | 0.1 m |
| 40 | Uracil | 5.0μ |
| 41 | Uridine | 20.0μ |
| 42 | L-Leucine | 0.2 m |
| 43 | L-Valine | 0.2 m |
| 44 | Thymidine | 20.0μ |
| 45 | Water | 55.4 |
| 46 | Hydrogen ions (pH 7.1) | 79.4 n |
| 47 | Oxygen (air saturation) | 0.2 m |
| 48 | L-Alanine | 0.2 m |
| 49 | L-Arginine | 0.1 m |
| 50 | D,L-Carnithine chloride (BT) | 50.0μ |
| 51 | L-Carnosine | 5.0μ |
| 52 | L-Cysteine | 0.2 m |
| 53 | L-Glutathione reduced | 3.0μ |
| 54 | Glycine | 0.2 m |
| 55 | L-Histidine | 0.1 m |
| 56 | L-Hydroxyproline | 10.0μ |
| 57 | L-Lysine-HCl | 0.2 m |
| 58 | L-Methionine | 0.1 m |
| 59 | D,L-Mevalolactone | 5.0μ |
| 60 | Nicotinic acid amide | 20.0μ |
| 61 | L-Ornithine-HCl | 50.0μ |
| 62 | D-Ca—pantothenate (B5) | 5.0μ |
| 63 | L-Proline | 0.1 m |
| 64 | Pyridoxal-HCl | 5.0μ |
| 65 | Pyridoxine-HCl (B6) | 2.0μ |
| 66 | Sarcosine | 50.0μ |
| 67 | L-Serine | 0.1 m |
| 68 | Taurine | 0.1 m |
| 69 | Thiamine-HCl (B1) | 5.0μ |
| 70 | L-Threonine | 0.2 m |
| 71 | Vitamin B 12 | 0.5μ |
| 72 | Vitamin U | 1.0μ |
| 73 | Adenine | 50.0μ |
| 74 | Folic acid (Bc) | 5.0μ |
| 75 | Guanine | 5.0μ |
| 76 | Guanosine | 20.0μ |
| 77 | Hypoxanthine | 5.0μ |
| 78 | Rutin (Vitamin P) | 5.0μ |
| 79 | Xanthine | 5.0μ |
| 80 | Ethanol (60 μl/l) | 1.0 m |
| 81 | Cholesterol | 1.0μ |
| 82 | Ergocalciferol (D2) | 0.5μ |
| 83 | D,L-χ-Lipoic acid | 2.0μ |
| 84 | Menadione (K3) | 0.2μ |
| 85 | D,L-χ-Tocopherol acetate (E) | 1.0μ |
| 86 | Coenzyme Q 10 ubiquinone 50 | 0.1μ |
| 87 | 3-Phytylmenadione (K1) | 0.2μ |
| 88 | Retinol acetate (A) | 1.0μ |
| 89 | Linolenic acid (F) | 5.0μ |
| 90 | Linoleic acid (F) | 1.0μ |
| 91 | Oleic acid | 5.0μ |
| 92 | Penicillin G | 80.0μ |
| 93 | Streptomycin | 80.0μ |
| 94 | Activator(s) (CON A) | 50.0 n |

Dependent on the type of desired product, either mixed populations of leukocytes or homogenous leukocyte types are cultured. The preparation and culture of leukocytes must be performed under sterile conditions. Culturing is performed for a period sufficiently long to obtain a satisfactory mediator level. A suitable period of time is 10 to 50 hours. Shorter periods result in lower mediator yields and the process is thus not economical.

On the other hand, the medium is used up after a culture period of 50 hours and the cells begin to die. An increase of the yield can therefore not be obtained in this case, except in the case of subculturing of cells and renewal of the culture medium.

The leukocytes are cultured at a temperature of about 30° to 42° C., preferably at about 37° C. At lower temperatures the culture process is not satisfactory, while at temperatures of above 42° C. the luekocytes are damaged.

Culturing is carried out at a concentration of about $10^6$ to $5 \times 10^8$ cells/ml, preferably $10^7$ to $10^8$ cells/ml. At lower cell concentrations the mediator yield per volume unit of the culture solution is too low. With too large culture volumes, the process is not economical. At cell concentrations of above $5 \times 10^8$ cells/ml, nutrition of the cells in the medium becomes rapidly inefficient.

Culturing can be carried out in normal atmosphere. Preferably increased carbon dioxide partial pressure is maintained during culturing. This pressure can amount to about 10 vol%. 2 vol% are preferred. The oxygen supply to the culture is of great importance. Oxygen can be supplied e.g. by bubbling air through the culture. To avoid contamination of the culture, the air is preferably sterilized and heat-decontaminated, i.e. it is freed of endotoxins and other organic constituents. The cell suspension is stirred or agitated during culturing.

Certain types of the inventive chemorecruitins are already obtained in satisfactory yields by normal culture of leukocytes or certain leukocyte types. The GMR, for instance, is obtained in high yields by culturing mixed populations of leukocytes or homogenous populations of granulocytes under the above-indicated conditions.

Other types of chemorecruitins of the invention, however, are only formed in small amounts by normal culture of leukocytes or certain leukocyte types. This applies for instance to the chemorecruitins of mononuclear cells, such as MMR and MLR. To produce them in higher yields, it is necessary to stimulate the cells in culture to mitosis. Possible mitosis-inducing influences are the addition of polyvalent mitogens, endotoxin-mitogens and immune reactions on the cell surface of sensitized cells. Examples of suitable mitogens are lectins, in particular those of Canavalia ensiformis (Concanavalin A=CON). The mitosis-inducing factor CON is added as a solution to the culture medium.

To terminate culturing, the leukocytes are centrifuged from the supernatant culture solution which is subsequently processed for the resulting chemorecruitins. To avoid damaging the cells and thus contamination of the culture solution with cell particles, the culture is centrifuged at relatively low speed, i.e. at about 300 to $400 \times g$. After removal of the major part of the cells from the supernatant, it is expedient to centrifuge the latter again at a higher speed. In this way, the remaining floating particles are removed. The separated leukocytes can either be cultured again, cryo-preserved or used for other biotechnical purposes.

The supernatant culture solution freed from the cells contains the secretion products of the cultured leukocytes. These include the chemorecruitins of the invention and a number of other proteins and other substances. Their concentration in the culture solution is approximately within the nanomolar range. Consequently, a yield of about 1 to 10 mg of a defined mediator requires a culture solution volume of about 1000 l with respect to a 10% recovery after purification. As regards the number of cells to be used it can be calculated that in view of the molecular efficiency of the cells, about $10^{14}$ leukocytes are necessary for obtaining a quantity of about 100 nmol proteins. This corresponds to about 1 mg of a mediator with the molecular weight of 10,000 dalton. This means that for the isolation of mediators in physical amounts about 50 kg of leukocytes are necessary for the culture. For reasons of availability, leukocytes of man, cow, horse, pig, sheep, dog, cat, rabbit, rat, mouse or guinea pig are preferred. The process described in the German unexamined patent publication DE-OS No. 30 09 126 is especially suitable for the preparation of large amounts of leukocytes; see also J. H. Wissler et al., Hoppe-Seyler's Z. F. Physiol Chemie. 361 (1980), p. 351 to 352.

Apart form leukocyte cultures, the chemorecruitins of the invention can also be obtained from inflamed tissue sites. There, they are formed by the accumulation of leukocytes in the course of inflammatory processes induced by tissue injuries. The inflamed tissue can be obtained in the usual manner and used for the preparation of the chemorecruitins. Inflamed tissues are homogenized in buffer solution and soluble constituents or exudates are separated from insoluble structural components by means of centrifugation.

Preferably, inflamed, infarcted heart mucle tissue is used which was formed by ligation of 24 hours of the left anterior descendent branch of the left coronary artery by a transfemoral catheter technique. The leukocyte-containing inflamed heart muscle site is separated at 0° to 4° C. from the remaining non-infracted tissue.

As shown above, the preparation and isolation of the chemorecruitins of the invention requires the processing of a very large culture solution volume. Therefore, at the beginning of the purification process effective reduction of the solution volume to be processed is necessary. In addition to the small amounts of the proteins produced, the culture solution contains the mixture of the components of the medium. Preferably, in the first step of the purification process a separation of the formed proteins from the medium components with a concomitant reduction of the large volume of aqueous solution is achieved. This can be effected by selective salting-out precipitation of the proteins from the supernatant culture solution, for instance by adding a sulfate or a phosphate. In the following, the salting-out precipitation of proteins is exemplified by adding ammonium sulfate to the culture solution.

By saturation of the supernatant culture solution with ammonium sulfate, a major portion of the proteins formed is precipitated together with serum albumin present as medium component. The proteins precipitated are recovered e.g. by centrifugation. They are then separated into the individual components of the mixture as described below. Thereby, some chemorecruitins are obtained. On the other hand, some other chemorecruitins are salt-soluble and remain in the supernatant solution of the salting-out precipitation process. This supernatant also contains all soluble components of the medium. It is concentrated and the proteins obtained are processed in the manner described below.

If the protein-containing supernatant culture solution is saturated with ammonium sulfate, a major portion of proteins is precipitated. In this way, a protein mixture is obtained consisting of numerous different proteins. Their separation into the individual protein components is obviously laborious. Therefore, in a preferred embodiment of the inventive process the protein mixture of the supernatant culture solution is already separated into several fractions by the salting-out precipitation step. The separation into several crude protein fractions is possible, since groups of individual proteins precipitate at different ammonium sulfate concentrations. Preferably, in the process of the invention, ammonium sulfate is therefore added stepwise to the culture solution up to a specific degree of saturation. Each fraction contains a group of proteins, the solubility product of which corresponds to the range of salt saturation. Hence, in the process according to the invention a crude separation into groups of proteins can be achieved in this first step by suitable choice of the saturation limits.

For instance, the supernatant culture solution is first brought to a 35% saturation with ammonium sulfate. The protein precipitate obtained is separated off. The 35% saturation of the supernatant solution is then increased to 45% by further addition of ammonium sulfate. A protein precipitate is again formed which is separated off. Thereafter, the 45% salt-saturated supernatant solution is brought to a 90% ammonium sulfate saturation. The protein precipitate formed is again separated off. The supernatant solution of this precipitate is concentrated e.g. by dehydration dialysis or ultrafiltration.

The salting-out precipitation of proteins is preferably carried out at a temperature of about 0° to 10° C., especially of about 0° to 4° C. The subsequent purification steps are performed under the same conditions. The solutions used for the purification have a pH value of between 5 and 9, in particular between 6 and 8. In order to achieve a constant pH-value of the solution, a strong buffer, for instance 0.1 mol/l of phosphate buffer is preferably added prior to the salting-out precipitation. To maintain the redox potential of the proteins, cysteine is preferably added in an amount of 0.001 mol/l to all solutions throughout the process. The protein purification does not require sterile conditions.

After dissolution in a protein-compatible medium, the proteins obtained by salting-out precipitation can be directly subjected to purification and separation in the manner described below. The 90% salt-saturated supernatant of the last precipitation step is concentrated. For instance, by dehydration dialysis or ultrafiltration, all compounds having a molecular weight higher than about 300 to 500 daltons are obtained as a retentate fraction. They can also be further processed for purification of salt-soluble chemorecruitins.

The protein fractions obtained in the step described above contain the chemorecruitins of the invention in admixture with numerous foreign proteins, e.g. other secreted proteins, in part serum albumins and in part CON. These foreign proteins form the major part of the constituents of this mixture. The chemorecruitins must be further purified by a sequence of further purification steps. Foreign proteins must be removed to avoid interference with the molecular-biological specifity of chemorecruitins. In addition, chemorecruitins themselves form a class of protein compounds which must be separated into individual, specifically acting structures.

In general, purification processes for proteins and other natural substances comprise sequences of combined separation techniques. Subtle differences in molecular size, charge, form, structure stability and nature of the molecular surfaces between the desired natural substance and the accompanying inactive foreign materials are used in such purification steps for their separation. Accordingly, a large number of combinations of various modifications of preparation techniques can be devised for the purification of a protein. The nature and the conditions of the preparation steps used, but also their sequential combination, are of paramount significance for operational properties, technical practicability, possibility of optional automatization and for the economical performance of a purification process and also for the yield and molecular quality of a natural product investigated. Particular attention has to be given to the optimum form of separation steps and on their ingenius combination into a purification sequence within the framework of structural and functional stability and other molecular parameters of the substance under investigation. This implies that the use of identical or similar separation principles (molecular sieve filtration, dialysis, ion exchange adsorption, etc.)—however in a different combination—can be of specific and paramount importance for the practice and economical performance of the purification process as well as for the yield and quality of the product obtained. In some cases, the use or omission of a single technique (.e.g. hydroxyapaptite chromatography, zone precipitation chromatography, etc.) at a certain point in the purification sequence or within a partial sequence, is of decisive significance for the yield and quality of the desired natural product as well as for the practice and economical performance of the purification process. These general relationships and basic principles inherent to the purification processes of natural products are clearly illustrated e.g. by some well known facts. Thus, within an economically and technically operable process for the purification of a natural product, initial dialysis, ultrafiltration or lyophilization steps are not recommended prior to reduction of original volumes of crude starting extracts by a factor of at least 500 to 1000 through other techniques.

For the purification of the individual protein fractions, a plurality of purification steps so far known in biochemistry can be used. Examples of such purification steps are: Preparative and analytical molecular sieve chromatography, anion and cation exchange chromatography and batch adsorption techniques, chromatography on hydroxyapatite, zone precipitation chromatography and recycling or cascade molecular sieve filtration.

It is possible to remove a considerable amount of accompanying foreign proteins from chemorecruitins by only one performance of these purification methods. However, proteins contained in the fractions tend to adhere together very strongly. Therefore, for example, in spite of different molecular weights of proteins, using molecular sieve filtration, no complete (ideal) separation of protein polyelectrolytes according to their exact molecular weight is obtained immediately. Hence it is necessary to perform at least two of the mentioned separation processes in sequence. A particularly preferred embodiment of the process in accordance with the invention uses three of the mentioned purification steps in sequence for the purification of chemorecruitin activity from the protein fractions.

All combinations of the mentioned separation steps constitute objects of the invention. It is evident, that certain sequences of separation steps are of less advantage than other combinations. Thus, for example, it is imperative to perform a preparative molecular sieve filtration before an analytical molcular sieve filtration:

In reverse order of performance, difficulties in handling, economic efficiency and yield are obvious.

Molecular sieve filtration achieves separation of proteins according to their molecular weights. Since the bulk of the foreign proteins have molecular weights different from those of chemorecruitins they can be separated off in this manner. A hydrophilic water-swelling molecular sieve as matrix is used for separation of the proteins by molecular weight. Examples of suitable molecular sieve matrices are dextrans cross-linked with epichlorohydrin (Sephadex), agaroses cross-linked with acrylamides (Ultrogels), and three-dimensionally cross-linked acrylamides (Biogels). The exclusion limits of the matrices used are higher than the separation limits.

If several separation steps are used, the molecular sieve filtration is preferably carried out as one of the first separation steps. Depending on the length-to-diameter ratio of the column used and the particle diameter of the gel matrix, molecular sieve filtration is termed "preparative" or "analytical". A molecular sieve filtration is "preparative" when the chromatography is performed on columns with a length-to-diameter ratio of up to 10:1 and a charge of the column of up to $\frac{1}{3}$ of its capacity in terms of the total separation volume of the matrix. "Analytical" molecular sieve filtration means a length-to-diameter ratio larger than 10:1, and preferably about 50:1, and a maximum charge of the column of up to 3% of its capacity.

In preparative molecular sieve chromatography, gel matrices with the largest possible particle size are used for maximum flow-through rates of mostly viscous protein solutions applied at reasonably low pressures. In analytical molecular sieve filtration the particle size ranges of the gel matrix are selected as small as possible, to obtain a maximum number of theoretical plates, a flow rate of the mobile phase in the range of 2 to 4 cm/h combined with a pressure which is limited to technical and safety aspects. These parameters are dependent on the structure of the gel matrix and may vary from gel to gel.

If several preparative molecular sieve filtrations are performed in sequence, graduated separation limits can be selected. This can be followed by an analytical molecular sieve filtration with correspondingly graduated separation limits. The exclusion limit of the gel used must in all cases be higher than about 10,000 daltons to allow a volume distribution of chemorecruitins between the stationary gel matrix phase and the mobile aqueous buffer phase.

The "exclusion limit" is a hydrodynamic parameter of a dissolved particle, which corresponds to the pore size of the gel matrix. Particles with a greater hydrodynamic parameter cannot penetrate the gel matrix (volume distribution coefficient $K_D=0$). The "separation limit" refers to a hydrodynamic parameter which has been chosen for the separation of dissolved particles from others and which has a value of between the volume distribution coefficient $K_D=0$ and $K_D=1$.

For molecular sieve filtration, the proteins are applied to the molecular sieve after dissolution in a protein-compatible liquid. A special example of a suitable solvent is 0.003 mol/l sodium-potassium phosphate solution containing 0.3 mol/l NaCl and 0.001 mol/l cysteine and having a pH of 7.4. After filtration, the chemorecruitin-containing fractions are concentrated in the manner described below and optionally subjected to a further purification step.

Examples of suitable anion exchangers are dextran matrices cross-linked with epichlorohydrin (Sephadex) or cellulose matrices carrying functional groups with anion exchanger capacity. These exchangers can be regenerated for repeated further use. It is preferable to use a weak anion exchanger in the Cl$^-$ form such as DEAE-Sephadex A-50, pre-swollen and equilibrated in a buffer. Swelling and equilibration is preferably carried out at a pH of 8 to 10. A special example of such a buffer solution is 0.01 mol/l tris-HCl containing 0.04 mol/l NaCl and 0.001 mol/l cysteine and having a pH value of 8.0.

The anion exchanger is added to the protein fraction in an amount sufficient for complete adsorption of the chemorecruitins and of the other positively adsorbing accompanying proteins. Two volume parts of swollen anion exchanger per volume of concentrated protein solution are normally sufficient. The reaction can be carried out either as chromatographic process or as an easy and fast batch adsorption technique. In the latter case, the supernatant liquid containing negatively adsorbed proteins is separated from the anion exchanger which is charged with the positively adsorbed chemorecruitins or other proteins, e.g. by filtration in a chromatographic column, by decantation or centrifugation. The charged anion exchanger is freed from adhering negatively adsorbing compounds by washing with water or a salt solution having a maximum ionic strength equivalent to 0.04 mol/l NaCl, preferably at a pH of 8 to 10.

The maximum preferred temperature is about 15° C. A special example of salt solution suitable for the washing-out process is the tris-HCl buffer of pH 8.0.

The anion exchanger on which chemorecruitins and other proteins are adsorbed and which is freed from the negatively adsorbed compounds is eluted with a protein-compatible aqueous salt solution having an ionic strength higher than 0.04 mol/l NaCl and a pH of between 4.0 and 10.0. A salt solution of high ionic strength and a pH of between 5.0 and 7.0 is preferably used. A special example of such a salt solution is a 2.0 mol/l NaCl solution buffered to a pH of 6.5 with 0.01 mol/l piperazine-HCl and containing 0.001 mol/l cysteine.

If the anion exchange reaction is carried out as a chromatographic process, elution of the chemorecruitins and other positively adsorbed proteins can also be done by a linear NaCl concentration gradient.

Examples of cation exchange matrices suitable for the purification of the protein fraction are dextrans cross-linked with epichlorohydrin (Sephadex) or cellulose matrices carrying functional groups with cation exchange capacity. These can be readily regenerated after use and employed again. It is preferable to use a weakly acidic cation exchanger such as CM-Sephadex C-50 having Na$^+$ as mobile counter-ion, and to perform the exchange reaction at a pH between 4 and 6. To facilitate the charge process and to approach more ideal equilibria conditions prior to treatment with the cation exchanger the protein fractions should be diluted with a protein-compatible salt solution having a maximum ionic strength equivalent to 0.04 mol/l NaCl. This salt solution can be used at the same time to adjust the pH. A special example of a salt solution for this purpose is a 0.001 mol/l potassium phosphate-acetate buffer containing 0.04 mol/l NaCl and 0.001 mol/l cysteine and having a pH of 4 to 6. This cation-exchange reaction may be performed as a chromatographic process, or technically easier, as a batch process.

The swollen cation exchanger is added to the protein fraction in a quantity sufficient to adsorb it. As a rule, about 2 volume parts of swollen ion exchanger per volume part of protein solution is sufficient for this purpose. The supernatant is then separated from the cation exchanger charged with proteins, for example by decantation or centrifugation. The charged cation exchanger is freed from adhereing, negatively adsorbed compounds by washing with water or a salt solution, having a maximum ionic strength equivalent to 0.04 mol/l NaCl. Preferably a pH of about 4 to 6 and a maximum temperature of about 15° C. is used. A special example of a salt solution suitable for the washing out process is the mentioned potassium phosphate-acetate buffer having a pH of 5.0.

The washed protein-charged cation exchanger is now eluted with a protein-compatible aqueous salt solution. A salt solution of high ionic strength with a pH of about 4 to 10 is preferably used for this purpose. Special examples of such salt solutions are aqueous 0.5 mol/l potassium phosphate with a pH of 6.5 to 7.5 or a 2 to 5 mol/l NaCl with the same pH.

For chromatography on hydroxyapatite, salts, e.g. ammonium sulfate and especially phosphates, possibly present from preceding steps are removed from the protein solution, preferably by dialysis or ultrafiltration at membranes with an exclusion limit of 500 daltons prior to the application of the proteins to hydroxyapatite. Apart from viscosity increase by accompanying salts, however, only the phosphate concentration of the protein solution is critical for the chromatography on hydroxyapatite. The chemorecruitins are eluted by a potassium phosphate concentration gradient which is preferably linear. The chemorecruitin-containing fractions are collected and then concentrated in the manner described below.

The use of hydroxyapatite is of essential significance for the structure-conserving isolation of pure chemorecruitins. However, in general, for technical and economic reasons, considerable difficulties arise from chromatography of larger volumes of protein solutions on hydroxyapatite columns. On the one hand, larger protein amounts contribute to the strong tendency of hydroxyapatite to clog, thus becoming unusable as stationary matrix in chromatography. On the other hand, hydroxyapatite is very expensive. It use on larger scales is not economical. For these reasons, in the process of the invention, the separation of a large part of the accompanying foreign proteins by appropriate biotechnical purification steps from the chemorecruitin-containing protein fractions is preferred for considerably reducing the volume of the protein solution prior to its chromatography on hydroxyapatite.

In the zone precipitation chromatography (cf. J. Porath, Nature, vol. 196 (1962); p. 47–48), residual protein contaminations in the chemorecruitins are separated by salting-out fractionation of the proteins by means and along a salt concentration gradient. The basic principle of separation of proteins in zone precipitation chromatography are different, structure-related, reversible solubility characteristics of proteins. They belong to the most sensitive molecular separation criteria and are often used for demonstration of molecular homogeneity of a protein. Two variants of this technique for development of the chromatogram are known: Fractional precipitation zone chromatography and fractional elution zone chromatography. Both types of techniques may have selective advantages in specific cases as described for fractional precipitation and fractional elution methods in protein separation. Temperature and pH, column characteristics can all be varied within relatively wide limits.

The temperature for zone precipitation chromatography can be between 0° and 40° C. Preferably, a temperature range from about 0° to 10° C. is used, especially from about 4° to 6° C. The pH can be between 4 and 10; preferably, a pH range of 6 to 8 is used, especially a pH of about 7. The length-to-diameter ratio of the column used should be greater than about 10:1. A ratio of 30 to 100:1 and especially of about 50:1 is preferred. All protein-compatible salts having salting-out properties for proteins are suitable.

Examples of such salts are sodium-potassium phosphate, ammonium sulfate, and sodium sulfate. Ammonium sulfate is preferred.

The salt concentration gradient can have any desired shape provided that salting-out criteria of proteins achieve protein separation. Linear concentration gradients are preferred, especially an ascendent linear concentration gradient from 25 to 100% ammonium sulfate saturation. The maximum column charge is about 5% and preferably about 1% of total column volume.

The recycling or cascade molecular sieve filtration can be performed under the conditions described above for the analytical molecular sieve filtration. The same molecular sieves and the same column conditions can be used. Sephadex G 50 as stationary matrix is preferred in a column of a length-to-diameter ratio of at least about 50:1 and a maximum charge of about 3% of the column volume. The solvents used in the analytical molecular sieve filtration are also preferred as solvents for the elution in this method.

In recycling molecular sieve filtration, the distribution equilibria are disturbed continuously and the eluate is recycled onto the same column with fixed separation limits. In this way, the separation length of the migrating protein distribution bands are differentially extended. Alternatively, in cascade molecular sieve filtration, distribution equilibria are disturbed by continous transfer of the eluate into a new second column with the same or similar, defined parameters at fixed separation limits.

Between the above-described purification steps, and if necessary at any stage for special purposes, protein solutions can be separated and freed from unwanted salts and water as well as concomitantly concentrated. The concentration (separation of a major portion of aqueous salt solution of the protein) can be achieved in different ways. Dehydration dialysis or ultrafiltration against protein-compatible liquid, preferably a sodium potassium phosphate buffer, are such methods. Dehydration dialysis is carried out preferably against polyethylene glycol (molecular weight 20,000 daltons) at membranes with exclusion limits of preferably 500 daltons. Ultrafiltration is preferably achieved at membranes with an exclusion limit of about 500 daltons. Small amounts of protein precipitates formed are removed by intermediary centrifugation to result in a clear protein solution. A desalting molecular sieve filtration on matrices with appropriate separation and exclusion limits can as well be used for this purpose, e.g. on Sephadex G 10, G 15 or G 20 as matrices. Furthermore, by selecting an appropriate mobile phase in the usual way, a usual molecular sieve filtration step can also be used concomitantly for this purpose.

To prevent sulfhydryl group oxidation, about 0.001 mol/l of cysteine is preferably added to protein solutions throughout.

In the molecular sieve filtration purification steps about 0.4 mol/l ammonium sulfate is preferably added to the protein solution. In contrast to higher concentrations of this salt, at this concentration ammonium sulfate exerts a strong salting-in effect on proteins. Thus, proteins are better kept in solution during the molecular sieve filtration. Moreover, ammonium sulfate prevents growth of microorganisms and inhibits certain enzymes. Hence, it contributes to stabilization of the chemorecruitin structure which is important when chromatography is performed at higher temperature (above about 20° C.) and under nonsterile conditions.

Chemorecruitins which can be salted out are preferably completely precipitated alone or together with accompanying proteins by adding ammonium sulfate up to a concentration of about 3.25 to 3.7 mol/l (80 to 90% saturation). For this purpose 630 g/l ammonium sulfate are added (about 90% saturation). The pH value is preferably kept between 4 and 9 and the temperature up to 40° C., preferably between 0° and 8° C. The chemorecruitin-containing protein precipitate is separated from the protein-free supernatant solution by filtration, decantation or centrifugation. Unless otherwise stated, centrifugation is preferably carried out at least at 10,000×g for a minimum of 45 min, and preferably for 1 h, in a one-step process. Or it can be carried out in two stages, at lower forces in the first stage for removal of the bulk of precipitated proteins; and then, for the supernatant of the first stage containing residual fine protein particles at higher forces, e.g. 20,000 to 50,000×g, by flow-through centrifugation.

The temperature and pH conditions during performance of the purification steps are not particularly critical. If the native conformation of the protein is to be preserved, an optimum temperature range is about 0° to 8° C., and preferably about 0° to 4° C. Moreover, the separation and purification steps must be carried out under essentially physiological pH and salt conditions. An essential advantage of the process of the invention consists in that these conditions are for the first time easy to adhere to.

The chemorecruitin obtained can be stored in a buffered physiological saline, e.g. in 0.0015 mol/l sodium-potassium phosphate solution containing 0.15 mol/l (0.9 w/v%) NaCl, 0.001 mol/l cysteine and having a pH of 7.4. After usual sterilization by filtration (pore diameter 0.2 μm), the protein preparation remains native and biologically active at room temperature for at least 200 h or frozen at −25° C. for at least 5 years. This stability of the protein can be considered, among others, to be one of the criteria of molecular homogeneity. Chemorecruitin solutions are safely stored at temperatures of between −20° and +50° C. in the presence of 2.0 to 3.6 mol/l ammonium sulfate (50 to 90% saturation). At this high osmotic pressure chemorecruitin solutions are protected against infection and degradation by microorganisms and bacterial growth. For their physiological, therapeutical and any other use, the chemorecruitins are again freed from salts by dialysis or ultrafiltration against an appropriate saline as described above.

The invention will now be given in detail by examples describing the isolation of the chemorecruitin protein preparation starting from leukocytes of porcine blood. However, the invention is not restricted to this embodiment. Leukocytes and inflamed tissues of other mammalians can be used too.

EXAMPLE A

PREPARATION OF CHEMORECRUITINS FROM SUPERNATANTS OF CULTURES OF A MIXED POPULATION OF VIABLE LEUKOCYTES

The production of chemorecruitins in a culture solution of a mixed population of leukocytes and the separation of monocyto-leukorecruitin (MLR), granulocyto-metamyelorecruitin (GMR) and monocyto-metamyelorecruitin (MMR) from the other components of the culture supernatant are described. All process steps are carried out at 0° to 8° C. in the presence of 0.001 mol/l cysteine, unless otherwise specified. The centrifugation is carried out in the manner described, either as a one or two step procedure (as flowthrough centrifugation).

A 1 Preparation and culture of a mixed population of viable leukocytes 50 kg (about $10^{14}$) leukocytes are isolated as mixed cell population of physiological composition from 10,000 l of porcine blood and cultured in 20 batches of 2.5 kg (about $5 \times 10^{12}$ cells) under sterile conditions. The medium indicated in table V is used as culture solution. 50 l of culture medium are used per batch. Culturing is performed in glass vessels (Duran 50 or Pyrex glass). Initially, the cell density is about $10^8$ cells/ml. The culture is maintained at 37° C. in an atmosphere of 1 v/v % $CO_2$ over 40 hours. During this period, the cell suspension is slowly stirred (to r.p.m.) and flooded with sterile, water-washed and heat-decontaminated air bubbles (<1 mm). The heat-decontamination of air is performed at about 500° C. by flowing through a silica tube. In addition to the partial oxygen pressue, the pH value (7.1) and the D-glucose level are measured and maintained constant. During culturing, the cells are induced to mitosis by the polyvalent mitogen content (CON) of the culture medium. The number, differential and morphological viability (dye exclusion test) of the cells are continously determined by usual methods of hematology and cell culture techniques. The functional viability of cells is measured by their motility and their ability to respond to chemokinetic and chemotactic proteins. Mitoses are determined by chromosome count. The morphological viability of the cells after their biotechnical culturing is 95%. The entire loss in cells (mainly granulocytes) during culturing is at most 20% which is normal for primary cell cultures.

The culture is terminated by separating the cells from the supernatant solution by centrifugation for 10 minutes at 400×g and 10° C. The cells are washed twice in a salt solution containing 0.15 mol/l NaCl, 0.0015 mol/l sodium potassium phosphate and having the pH-value 7.1. They can be used for another purpose.

The culture supernatant solution is then centrifuged again for 1 hour at 10,000×g and at 4° C. to remove suspended particles. The resultant clear supernatant culture solution which has a total volume of 1000 liters and contains about 1,400 g protein as well as other macromolecules and salts is directly subjected to salting-out fractionation with ammonium sulfate (A2). Unless otherwise stated, all further steps are carried out at 0°–4° C.

A.2. First purification step (salting-out fractionation): Preparation of crude protein concentrate fractions 0.5 mol/l sodium-potassium phosphate buffer solution with a pH value of 6.7 is added to the supernatant culture solution (A 1) up to a final concentration of 0.1 mol/l. Furthermore, solid L-cysteine is added up to a concentration of 0.001 mol/l.

This buffered supernatant culture solution is then adjusted to 35% saturation of ammonium sulfate by addition of 199 g of ammonium sulfate/l solution. During the addition, the pH-value of the protein solution is continuously controlled and maintained at 6.7 by the addition of 2 n ammonia. Part of the proteins is precipitated from the solution. The protein precipitate formed is separated from the supernatant containing salt-soluble proteins by centrifugation for 1 hour at 10,000×g. The precipitated crude protein fraction I is obtained as ammonium sulfate-containing protein sludge which contains about 100 g protein. This crude protein concentrate fraction I may be separately processed for its constituents, according to the procedure described below for the crude protein concentrate fraction III.

Then the 35% salt-saturated supernatant culture solution is adjusted to 45% saturation of ammonium sulfate by adding 60 g of ammonium sulfate/l solution. The pH value of the protein solution is continuously controlled and maintained constant at 6.7 by 2 n ammonia. Another portion of proteins is precipitated from the solution. The protein precipitate is separated from the supernatant containing salt-soluble proteins by centrifugation for 1 hours at 10,000×g. The precipitated crude protein concentrate fraction II is obtained as ammonium sulfate-containing protein sludge, the protein content of which is about 60 g This crude protein concentrate fraction II may be separately processed for its constituents, according to the procedure described below for the crude protein concentrate fraction III.

The 45% salt-saturated supernatant culture solution is then adjusted to 90% saturation of ammonium sulfate by adding 323 g of ammonium sulfate/l of solution. The pH-value of the protein solution is again continuously controlled and maintained constant at 6.7 by 2 n ammonia. Another portion of the proteins is precipitated from the solution. The protein precipitate is separated from the supernatant containing salt-soluble proteins by centrifugation for 1 hour at 10,000×g. The precipitated crude protein concentrate fraction III is obtained as ammonium sulfate-containing protein sludge the protein content of which is approximately 1,080 g. This fraction also contains the bulk of the serum albumin as component of the culture medium. This crude protein concentrate fraction III is processed for chemorecruitins according to the procedure described below. The 90% salt saturated supernatant fraction IV of the crude fraction III contains 160 g of salt-soluble proteins and other macromolecules (<500 dalton).

This salt-soluble protein-containing supernatant fraction IV is diluted with the same volume of the buffer solution A (0.15 mol/l NaCl, 0.0015 mol/l sodium-potassium phosphate, 0.001 mol/l L-cysteine, pH 7.4) to 45% saturation of ammonium sulfate and a maximum phosphate concentration of 0.05 mol/l. This solution is concentrated and desalted by ultrafiltration at a membrane with an exclusion limit of 500 daltons as a maximum. The salt-soluble proteins of this solution are obtained as crude retentate fraction IV in a volume of 13 l (about 100-fold concentration).

The crude protein concentrate fractions I, II and III and the retentate fraction IV are further purified. The fine purification of fraction III is described below under A 3 and applies to all crude protein concentrate fractions. The fine purification of the retentate fraction is mentioned below under A 4. The crude protein concentrate fraction III contains the chemorecruitins GMR and MLR; the retentate fraction IV contains MMR.

A.3. Fine purification of chemorecruitins in the crude protein concentrate fraction III

A.3.1. Anion exchange chromatography

The crude protein concentrate fraction III obtained above (A 2) is dissolved in a minimum volume of buffer solution B (0.01 mol/l of tris-HCl solution containing 0.04 mol/l NaCl and 0.001 mol/l cysteine and having a pH value of 8.0). The resultant slightly turbid solution (20 l) is clarified by centrifugation and then freed of salts by dialysis at a membrane with the exclusion limit of 500 dalton against buffer solution B until no sulfate ions are detectable. The clear solution obtained is then applied to a column of a swollen regenerated anion exchanger ($Cl^-$ as mobile exchangeable ion). It has a dextran matrix cross-linked with epichlorohydrin (DEAE-Sephadex A 50) which is equilibrated in the above-mentioned buffer system B.

The column has four times the volume of the protein solution and a length-to-diameter ratio of 10:1. The gel column is then washed with the above-mentioned adsorption buffer solution B until the extinction of the filtrate at 280 nm is $\leq 1.0$.

For elution of the chemorecuritins and the adsorbed proteins, the charged ion exchanger gel is eluted with a NaCl-concentration gradient during 2 days. The gradient is linearly ascending from 0.04 to 2.0 mol/l NaCl, whereas the pH value, the tris/HCl and the cysteine concentrations are maintained constant. The same shape of gradient is then used for lowering the pH from 8 to 6.5 for further elution of the compounds. It is made up by 0.01 mol/l piperacine-HCl-buffer containing 2.0 mol/l NaCl and 0.001 mol/l cysteine and having the pH 6.5.

The chemorecruitin-containing fractions are collected separately (GMR and MLR are separated in this step). They are, therefore, separately processed in further purification steps described below (A.3.2–A.3.6)

A.3.2. Preparative molecular sieve filtration

After concentration of the proteins in the fractions (A.3.1) by salting-out precipitation with ammonium sulfate, the protein precipitate containing either GMR or MLR is dissolved in a minimum volume of buffer solution C (0.003 mol/l sodium-potassium phosphate containing 0.3 mol/l NaCl and 0.001 mol/l cysteine and having a pH value of 7.4). After removal of a small amount of insoluble compounds by centrifugation, the solution is applied to a column of a molecular sieve matrix of agarose crosslinked with acrylamide (Ultrogel AcA 34, particle size 60 to 160 μm) for preparative molecular sieve filtration. The column has 10 times the volume of the protein solution and a length-to-diameter ratio of 20:1. The column is then eluted with an upward flow (3 cm/h) of the mentioned buffer solution C. For GMR, the fraction with the separation limits of 20,000 and 10,000 dalton and for LMR, the fraction with the separation limits of 18,000 and 6,000 dalton are collected. For the concentration of the proteins, the fractions are lyophilized and ultrafiltrated at a membrane with the exclusion limit of 500 daltons or are adjusted to an ammonium sulfate concentration of 3.7 mol/l. In this case, the protein precipitates are separated from the supernatant by centrifugation and further processed as described below (A.3.3)

A.3.3 Cation exchange chromatography

The resultant GMR or MLR-containing protein precipitates (A 3.2) are dissolved in 1.5 volume parts of buffer solution D (0.01 mol/l sodium-potassium phosphate, 0.04 mol/l NaCl, 0.001 mol/l cysteine, pH 6.0). The solutions are centrifuged at 10,000×g for 1 hour for removal of a small amount of insoluble material.

The clear solution is dialyzed against the buffer solution D at a membrane with the exclusion limit of 500 dalton until no sulfate ions are detectable. The clear solution obtained is then applied to a column of swollen, regenerated cation exchanger based on a dextran matrix cross-linked with epichlorohydrin (CM-Sephadex C 50). The exchanger is equilibrated in the above-mentioned buffer system D ($Na^+$ as mobile exchangeable ion).

The column has four times the volume of the protein solution and a length-to-diameter ratio of 10:1. The gel column is then washed with the above-mentioned adsorption buffer solution D, until the extinction of the filtrate at 280 nm is ≦1.0.

For elution of the chemorecruitins and the adsorbed proteins, the charged ion exchange gel is eluted with an NaCl-concentration gradient during 2 days. The gradient is linearly ascending from 0.04 to 2.0 mol/l NaCl whereas the pH-value and the phosphate and cysteine concentrations are maintained constant. For further elution, the same shape of gradient is then used for increasing the phosphate concentration from 0.01 to 0.5 mol/l at a pH of 8.0, whereas the NaCl (2 mol/l) and cysteine concentrations are kept constant.

The GMR or MLR containing fractions are collected and concentrated in the usual manner and further processed as described below (A.3.4).

A.3.4 Chromatography on hydroxyapatite

The GMR or MLR-containing protein precipitates (A.3.3) are dissolved in a minimum volume of 0.0001 mol/l sodium-potassium phosphate buffer solution E containing 0.001 mol/l cysteine and having a pH of 7.20. The solutions are then desalted with this buffer by molecular sieve filtration, ultrafiltration or dialysis (exclusion limit 500 dalton), until no sulfate is detectable in the dialysis buffer. Thereafter, a small portion of insoluble material is removed by centrifugation at 10,000×g for 1 hour.

The clear GMR or MLR-containing protein solutions obtained are separately applied to a column of hydroxyapatite. The length-to-diameter ratio of the column is 10:1 and it has four times the volume of the protein volume to be applied. The column has been equilibrated with the mentioned buffer E used in an amount five times the column volume (flow 3 cm/h).

The negatively adsorbed proteins are washed out with the buffer solution E used for equilibrating the column. The elution of the GMR or MLR-containing fractions is carried out with a phosphate concentration gradient for 4 days. The gradient is linearly ascending from 0.0001 mol/l to 0.5 mol/l sodium-potassium phosphate having a constant pH value of 7.4 and constant cysteine concentration. GMR is eluted at an average phosphate concentration of about 0.1 mol/l, whereas MLR is eluted at about 0.003 mol/l. The elution gradient is measured and controlled by means of conductivity. The GMR or MLR-containing fractions are concentrated in the usual manner and further processed as described below (A.3.5.).

A.3.5. Zone precipitation chromatography

The GMR or LMR-containing fractions (A.3.4.) are dissolved in 0.1 mol/l NaCl, 0.001 mol/l cysteine and 1 mol/l ammonium sulfate and having a pH value of 7.4. The resultant solution is applied at a temperature of 4° C. to a column of swollen molecular sieve matrix of dextran cross-linked with epichlorohydrin (Sephadex G-25). In the matrix, an ascendent, linear ammonium sulfate concentration gradient is established with the mobile buffer phase from 1.0 to 4.0 mol/l ammonium sulfate (25 to 100% saturation). The slope of the gradient is +2% of the ammonium sulfate saturation/cm of column height (0.08 mol/l $(NH_4)_2SO_4$/cm). The range of the gradient extends over approximately half the length of the column.

The length-to-diameter ratio of the column is 50:1, the column volume is 100 times higher than the protein solution volume to be applied. The flow rate is 2 cm/h.

The elution is carried out with the above-mentioned sodium-potassium phosphate solution F containing 1 mol/l of ammonium sulfate. The GMR or MLR-containing fractions which are eluted at 58% and 67% ammonium sulfate saturation, respectively, are collected. The proteins are concentrated in the usual manner and further processed as described below (A.3.6).

A.3.6. Analytical recycling molecular sieve filtration

The GMR or MLR-containing fractions (A.3.5.) are dissolved in buffer C (0.003 mol/l sodium-potassium phosphate containing 0.3 mol/l NaCl and 0.001 mol/l casteine and having a pH value of 7.4). Removal of a small portion of insoluble substances is achieved by centrifugation for 30 minutes at 48,000×g.

The resultant clear solution is then subjected to analytical recycling molecular sieve chromatography. For this purpose, the solution is applied at a temperature of 4° C. to a column of Ultrogel AcA 44 having a particle size of 60 to 140 μm. The column has 50 times the volume of the protein solution and a length-to-diameter ratio of 50:1. The elution is carried out with the mentioned buffer C. The eluates are recycled three times at separation limits of either 17,000 dalton (GMR) or 14,000 dalton (MLR). After usual protein concentration, approximately 5 mg of GMR and 8 mg of MLR are obtained. The two chemorecruitins have a molecular homogeneity of >95%, as indicated by conventional methods.

A.4. Fine purification of chemorecruitins in the retentate fraction IV

The retentate fraction IV (A.2) is purified in the manner described above the crude protein concentrate fraction III. However, the sequence of the steps of preparative molecular sieve filtration and anion exchange chromatography is exchanged. Moreover, in the preparative molecular sive filtration and in the analytical recycling molecular sieve filtration, the Ultrogel AcA is replaced by a molecular sieve matrix of dextran which is cross-linked with epichlorohydrin (Sephadex G-50) and has a particle size of 40 to 120 and 20 to 80 μm, respectively.

In the preparative molecular sieve filtration, the separation limits are 12,000 to 3,000 dalton. In the chromatography on hydroxyapatite the MMR is eluted at an average phosphate concentration of 0.001 mol/l. In the zone precipitation chromatography, the MMR is eluted in the front distribution. In the analytical recycling molecular sieve filtration, the eluate is recycled at a separation limit of 8,500 dalton. The MMR yield is about 8 mg and has a molecular homogeneity of >95%, as shown by conventional methods.

In the following flow sheet, the above-described process for preparing the chemorecruitins of the invention is schematically represented.

mately 0.03 mg of MMR, 0.02 mg of MLR and about 0.01 mg of GMR.

EXAMPLE D

Preparation of Chemorecruitins From Leukocyte Homogenates

Leukocytes are prepared from blood according to example A. A homogenate of 500 g of leukocytes is prepared as shown in example C. for muscle tissue. The isolation of the chemorecruitins contained in the leukocytes is performed according to example A. The leukocytes cultured without stimulation contain only relatively small (about 1%) amounts of monocyte-chemore-

| FLOW SHEET FOR BIOTECHNICAL PURIFICATION OF LEUKOCYTE - DERIVED CHEMORECRUITINS | | |
|---|---|---|
| STEP | ↓ | STERILE CELL CULTURE |
| 1st | ↓ | CELL CULTURE SUPERNATANT |
| 2nd | ↓ | SALTING-OUT PRECIPITATION WITH AMMONIUM SULFATE |
| | ↓ 90% SATURATION FRACTION | ↓ >90% SATURATION FRACTION (SOLUBLE) |
| 3rd | ↓ ANION EXCHANGE CHROMATOGRAPHY | ↓ ULTRAFILTRATION, EXCLUSION >500 d |
| 4th | ↓ MOLECULAR SIEVE FILTRATION | ↓ MOLECULAR SIEVE FILTRATION |
| 5th | ↓ CATION EXCHANGE CHROMATOGRAPHY | ↓ ANION EXCHANGE CHROMATOGRAPHY |
| 6th | ↓ HYDROXYAPATITE CHROMATOGRAPHY | ↓ CATION EXCHANGE CHROMATOGRAPHY |
| 7th | ↓ ZONE PRECIPITATION CHROMATOGRAPHY | ↓ HYDROXYAPATITE CHROMATOGRAPHY |
| 8th | ↓ CASCADE MOLECULAR SIEVE FILTRATION | ↓ ZONE PRECIPITATION CHROMATOGRAPHY |
| 9th | ↓ | ↓ CASCADE MOLECULAR SIEVE FILTRATION |
| | MONOCYTO-LEUKORECRUITIN GRANULOCYTO-METAMYELORECRUITIN | MONOCYTO-METAMYELORECRUITIN |

EXAMPLE B

Preparation of Chemorecruitins From Supernatants of Cultures of Viable Monocytes 3.5 kg (about $7 \times 10^{12}$) monocytes obtained from porcine blood are cultured under the conditions described in example A. During culture, the polyvalent mitogen (CON) in the medium induces the mitosis of the cells.

The chemorecruitins MMR and MLR secreted to the culture solution are isolated according to the procedure described in example A. They are thereby obtained in a highly purified state. The yields obtained are comparable to those of example A.

EXAMPLE C

Preparation of Chemorecruitins from Inflamed Tissue Sites

The preparation and isolation of chemorecruitins from inflamed tissue are described. 500 g of infarcted, inflamed canine heart muscle tissue are used. The heart muscle tissue is ground at 0°–4° C. 0.05 mol/l sodium potassium phosphate buffer solution containing 0.001 mol/l cysteine and having a pH of 6.8 is added in a quantity three times the amount of the tissue. The resultant suspension is homogenized in a homogenizer (ultraturax). Thereafter, the supernatant containing the soluble compounds of the inflamed tissue is separated from the insoluble constituents by centriguation at $10,000 \times g$ and 4° C. The resultant supernatant solution is then centrifuged for 3 hours at $100,000 \times g$. The clear supernatant solution obtained is siphoned off from the flotating lipid layer.

The chemorecruitin-containing clear supernatant protein solution is then subjected to fractional salting-out precipitation with ammonium sulfate according to example A. The resultant protein fractions I, II, III and the concentrated retentate fraction IV are processed as described in example A. From the 500 g tissue, chemorecruitins are obtained in a yield of approxicruitins (MMR and MLR). The yields are approximately 5 μg of GMR, 1 μg of MMR and about 1 μg of MLR.

What is claimed is:

1. Leukocyte derived chemorecruitin, characterized by the following properties:
   (a) biological activities in vivo and in vitro:
      specific induction of selective positive leukocytosis and/or leftward shift reactions by recruitment of mature and juvenile leukocytes from the bone marrow into the blood in vivo and in vitro;
      positive mobilization of mature and juvenile leukocytes directly from the bone marrow in vitro (also in blood-free systems, for instance cell culture and salt solutions);
      they are substantially free of other biological effects;
   (b) physico-chemical properties:
      no protein quaternary structure in the form of physically bound peptide subunits: each of the native proteins consists of only one peptide unit;
      electrophoretic migration in acrylamide matrices at a pH of 7.40 is anodic;
      soluble in aqueous media including in 15% ethanol at a pH value of at least 4.0 to 10;
      constant temperature coefficient of solubility in ammonium sulfate solutions between −10° C. and +50° C.;
      they contain, amongst others, the amino acids tyrosine, phenylalanine, alanine, glycine, lysine, valine, glutamic acid, arginine, leucine;
      they adsorb reversibly in structure and biological activity on anion and cation exchangers, calcium phosphate gel and hydroxyapatite and can be subjected in native form to volume partition chromatography.

2. Chemorecruitins according to claim 1, obtainable from leukocytes, by culturing leukocytes and isolation from the supernatant culture solution or from inflamed tissue.

3. Chemorecruitins according to claims 1, characterized in that they recruit a mixed leukocyte population into the blood.

4. Mononuclear leukocyte derived chemorecruitin (monocyto-leukorecruitin) according to claim 3 characterized by the following properties:
   (a) biological effects in vivo:
      induction of prolonged, strong leukocytosis reactions with leftward shift reaction and a late monocytosis and eosinophilia phase according to FIG. 1;
   (b) physico-chemical properties:
      molecular weight of the native protein (primary structure); approximately 12,000 dalton;
      insoluble in an ammonium sulfate solution at 90% saturation (3.6 mol/l);
      absorption spectrum (UV, visible and near IR-range) as given in FIG. 2.
      extinction coefficients according to the following Table I:

TABLE I

| Wave length, nm | $E_1$ mg/ml, 1 cm $(H_2O, 20°\ C.)$ ± 6% |
|---|---|
| 250 (min) | 0.28 |
| 260 | 0.38 |
| 270 | 0.55 |
| 280 (max) | 0.68 |
| 290 | 0.48 |
| 400–1000 | 0 |
| $E_{280}/E_{260}$ | 1.78 |

5. Chemorecruitins according to claim 1, characterized in that they recruit specific leukocyte types into the blood.

6. Chemorecruitins according to claim 5, characterized in that they recruit juvenile leukocyte forms of the granulocyte development line into the blood and optionally sequestrate the mature, adult cell types of this line.

7. Mononuclear leukocyte derived chemorecruitin (monocyto-metamyelorecruitin) according to claim 6, characterized by the following properties:
   (a) biological activities in vivo:
      induction of specific leftward shift reaction by recruitment of juvenile leukocytes and sequestration of mature leukocytes according to FIG. 3 and Table II;
      no general leukocytosis reaction;
   (b) physico-chemical properties:
      molecular weight of the native protein (primary structure): approximately 6,500 dalton;
      soluble in saturated ammonium sulfate solution (4.0 mol/l);
      absorption spectrum (UV, visible and near IR-range) according to FIG. 4;
      extinction coefficient according to the following Table III:

TABLE III

| Wave length, nm | $E_1$ mg/ml, 1 cm $(H_2O, 20°\ C.)$ ± 6% |
|---|---|
| 250 (min) | 0.23 |
| 260 | 0.32 |
| 270 | 0.50 |
| 280 (max) | 0.59 |
| 290 | 0.42 |
| 400–1000 | 0 |
| $E_{280}/E_{260}$ | 1.84 |

8. Granulocyte derived chemorecruitin (granulocyto-metamyelorecruitin) according to claim 6, characterized by the following properties:
   (a) biological activities:
      induction of leftward shift reaction with late, short-lasting monocytosis and weak leukocytosis reaction according to FIG. 5;
   (b) physico-chemical properties:
      molecular weight of the native protein (primary structure): approximately 15,000 dalton;
      insoluble in a 90% saturated ammonium sulfate solution (3.6 mol/l);
      absorption spectrum (UV, visible and near IR-range) as given in FIG. 6;
      extinction coefficient according to the following Table IV

TABLE IV

| Wave length, nm | $E_1$ mg/ml, 1 cm $(H_2O, 20°\ C.)$ + 6% |
|---|---|
| 252 (min) | 0.23 |
| 260 | 0.32 |
| 270 | 0.49 |
| 280 (max) | 0.62 |
| 290 | 0.44 |
| 400–1000 | 0 |
| $E_{280}/E_{260}$ | 1.92 |

9. A pharmaceutical composition for specifically influencing the defense state of the body of mammalians, comprising an effective amount of at least one highly purified chemorecruitin according to claim 1 and a suitable carrier therefor.

10. A pharmaceutical composition for specifically influencing the course of leukocyte recruitment in leukemia comprising an effective amount of at least one anti-chemorecruitin immunoglobulin and a suitable carrier therefor.

11. A method for specifically influencing the immune system of mammalians, comprising: administering an effective amount of at least one leukocytosis or leftward shift inducing chemorecruitin according to claim 1.

12. A method for specifically influencing the course of leukocyte recruitment in leukemia comprising administering an effective amount of at least one anti-chemorecruitin immunoglobulin.

13. A process for producing the leukocyte derived chemorecruitins of claim 1, which comprises:
   a. culturing luekocytes in a suitable culture medium;
   b. separating the cells from the culture medium after termination of culturing to yield a culture solution;
   c. prcipitating a first protein fraction from said culture solution by adding a sufficient amount of a suitable salt;
   d. adding a further amount of the salt to the supernatant to precipitate to obtain a second protein fraction;
   e. purifying the first and second protein fractions, to obtain chemorecruitins using preparative and analytical molecular sieve filtration, anion and cation exchange chromatography and batch adsorption processes, chromatography on hydroxyapatite, zone precipitation chromatography or recycling molecular sieve filtration.

14. The process according to claim 13, wherein a mixed leukocyte population is cultured.

15. The process according to claim 13, wherein a specific leukocyte type is cultured.

16. The process according to claim 13, wherein the leukocytes are cultured in a fully synthetic cell culture medium containing serum albumin as the only protein.

17. The process according to claim 13, wherein leukocyte mitosis is induced during culturing.

18. The process according to claim 17, wherein a polyvalent mitogen or endotoxin-mitogen is added or an immune reaction is promoted on the cell surface so as to induce leukocyte mitosis.

19. The process according to claim 18, wherein the mitosis of the leukocytes is induced by the addition of a lectin.

20. The process according to claim 19, wherein a lectin from Canavalia ensiformis (Concanavalin A=-CON) is used.

21. The process according to claim 16, wherein the leukocytes are cultured in a cell culture medium having the composition given in Table V.

22. The process according to claim 21, wherein the leukocytes are cultured for approximately 40 hours at a temperature of about 37° C., a concentration of about $10^7$ to $10^8$ cells/ml of culture solution, a $CO_2$ partial pressure of about 1%, while sufficient oxygen is supplied to the culture.

23. The process according to claim 13, wherein ammonium sulfate is used for salting out the proteins.

24. The process according to claim 13, wherein the ammonium sulfate concentration of the culture solution is stepwise increased and the proteins precipitated after each ammonium sulfate addition are separated thereby obtaining several crude protein fractions having graduated solubility at different ammonium sulfate concentration.

25. The process according to claim 24, wherein the ammonium sulfate concentration of the culture solution is adjusted stepwise to 35%, 45% and 90% saturation.

26. The process according to claim 13, wherein the supernatant of the precipitation after the separation of the protein precipitate is concentrated by ultrafiltration or dialysis.

27. The process according to claim 13, wherein at least two purification steps are performed in sequence.

28. The process according to claim 27 wherein at least three purification steps are performed in sequence.

29. A process for producing and isolating monocytoleukorecruitin which comprises:
   a. culturing a mixed leukocyte cell population or only monocytes;
   b. inducing cell mitosis during culturing by adding CON;
   c. terminating culturing;
   d. separating the cells from the culture medium after terminating culturing to yield a culture solution;
   e. adding ammonium sulfate to the culture solution up to a 90% saturation;
   f. separating the precipitated proteins from the ammonium sulfate containing supernatant;
   g. redissolving the precipitated proteins;
   h. purifying said proteins by anion exchange chromatography, preparative molecular sieve filtration, cation exchange chromatography, chromatography or hydroxyapatite, zone precipitation chromatography, and cascade molecular sieve filtration; and
   i. isolating the highly purified monocytoleukorecruitin from in the eluate of the cascade molecular sieve filtration by adding ammonium sulfate up to about 80–90% saturation and separating the precipitate from the supernatant.

30. A process for producing and isolating monocytometamyelorecruitin which comprises:
   a. culturing a mixed leukocyte cell population or only monocytes in a suitable culture medium;
   b. inducing the mitosis of the cells by CON during culturing;
   c. terminating culturing;
   d. separating the cells from the culture medium to yield a culture solution;
   e. adding ammonium sulfate to the culture solution up to a 90% saturation;
   f. separating the precipitated proteins from the ammonium sulfate containing supernatant;
   g. concentrating the supernatant;
   h. purifying the supernatant by preparative molecular sieve filtration, anion exchange chromatography, cation exchange chromatography, chromatography on hydroxyapatite, zone precipitation chromatography, and recycling molecular sieve filtration for removing the accompanyuing foreign proteins; and
   i. isolating the highly purified monocytometamyelorecruitin from the eluate of the recycling molecular sieve filtration by adding ammonium sulfate up to about 80–90% saturation and separating the precipitate from the supernatant.

31. A process for producing and isolating granulocytometamyelorecruitin which comprises:
   a. culturing a mixed leukocyte cell population or only granulocytes;
   b. inducing the mitosis of the cells by CON during culturing;
   c. terminating culturing;
   d. separating the cells from the culture medium to yield a culture solution;
   e. adding ammonium sulfate to the culture solution up to 90% saturation to precipitate proteins;
   f. separating the precipitated proteins from the ammonium sulfate containing supernatant;
   g. redissolving said proteins;
   h. purifying said proteins by anion exchange chromatography, preparative molecular sieve filtration, cation exchange chromatography, chromatography on hydroxyapatite, zone precipitation chromatography and recycling molecular sieve filtration for removing the accompanying foreign proteins; and
   i. isolating the highly purified granulocytometamyelorecruitin from the eluate of the cascade molecular sieve filtration by adding ammonium sulfate up to about 80–90% saturation and separating the precipitate from the supernatant.

32. The process according to any one of claims 13 and 24 to 31, wherein the soluble portion of a leukocyte or inflamed tissue homogenate is used instead of the culture solution of the leukocytes.

33. Lightly purified monocytoleukorecruitin.

34. Lightly purified monocytometamyelorecruitin.

35. Lightly purified granulocytometamyelorecruitin.

* * * * *